United States Patent [19]
Ali et al.

[11] Patent Number: 5,849,690
[45] Date of Patent: Dec. 15, 1998

[54] ANTI-AGGREGATORY PEPTIDES

[75] Inventors: Fadia El-Fehail Ali, Cherry Hill, N.J.; James Samanen, Phoenixville, Pa.

[73] Assignee: SmithKline Beecham Corporation, Philadelphia, Pa.

[21] Appl. No.: 918,487

[22] Filed: Jul. 22, 1992

Related U.S. Application Data

[60] Division of Ser. No. 335,306, Apr. 10, 1989, which is a continuation-in-part of Ser. No. 191,515, May 9, 1988, abandoned.

[51] Int. Cl.$^6$ ...................................................... C07K 4/00
[52] U.S. Cl. .................................................. 514/9; 514/11
[58] Field of Search .......................................... 514/9, 11

[56] References Cited

U.S. PATENT DOCUMENTS

| | | |
|---|---|---|
| 4,397,842 | 8/1983 | Goldstein et al. . |
| 4,517,686 | 5/1985 | Ruoslahti et al. . |
| 4,544,500 | 10/1985 | Bittle et al. . |
| 4,578,079 | 3/1986 | Ruoslahti et al. . |
| 4,589,881 | 5/1986 | Pierschbacher et al. . |
| 4,614,517 | 9/1986 | Ruoslahti et al. . |
| 4,661,111 | 4/1987 | Ruoslahti et al. . |
| 4,683,291 | 7/1987 | Zimmerman et al. . |
| 4,857,508 | 8/1989 | Adams et al. . |

FOREIGN PATENT DOCUMENTS

| | | |
|---|---|---|
| 204480 | 12/1986 | European Pat. Off. . |
| 265129 | 4/1988 | European Pat. Off. . |
| 275748 | 7/1988 | European Pat. Off. . |
| WO8400540 | 2/1984 | WIPO . |
| WO8803151 | 5/1988 | WIPO . |
| WO8905150 | 6/1989 | WIPO . |

OTHER PUBLICATIONS

D'Souza et al., J. Biol. Chem., 263, 3943 (1988).
Pierschbacher et al., J. Biol. Chem., 262, 17294 (1987).
Plow et al., Blood, 70, 110 (1987).
Ruggeri et al., Proc. Natl. Acad. Sci., 83, 5708 (1986).
Ginsberg et al., J. Biol. Chem., 260, 3931 (1985).
Plow et al., Proc. Natl. Acad. Sci., 82, 8057 (1985).
Haverstick et al., Blood, 66, 946 (1985).
Pierschbacher et al., Proc. Natl. Acad. Sci., 81, 5985 (1984).
Pierschbacher et al., Nature, 309, 30 (1984).
Yasuda et al., Clin. Res., 34, 2, 634A (1986).
Coller et al., Blood, 66, 1456 (1985).
Ohlstein et al., Thrombosis Research, 46, 575 (1987).
Aiken et al., Prostaglandins, 19, 629 (1980).
Ruoslahti et al., Science, 238, 491 (1987).
Nievelstein et al., Thromb. and Hemostasis, 58, 213 (1987).

*Primary Examiner*—Cecilia J. Tsang
*Assistant Examiner*—Patrick R. Delaney
*Attorney, Agent, or Firm*—Charles M. Kinzig; Edward T. Lentz

[57] ABSTRACT

This invention relates to compounds which are effective for inhibiting platelet aggregation, pharmaceutical compositions for effecting such activity, a method for inhibiting platelet aggregation and clot formation in a mammal, and a method for inhibiting reocclusion of a blood vessel following fibrinolytic therapy.

22 Claims, 3 Drawing Sheets

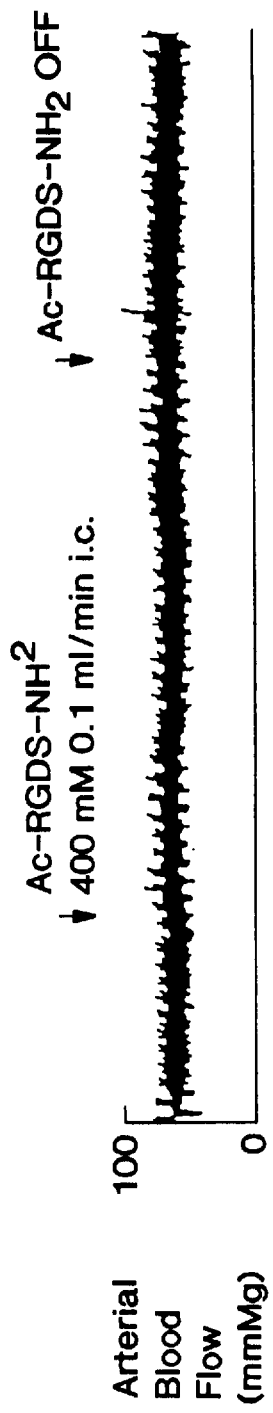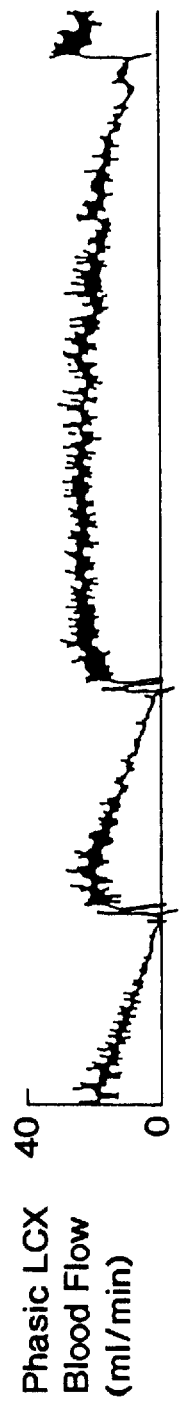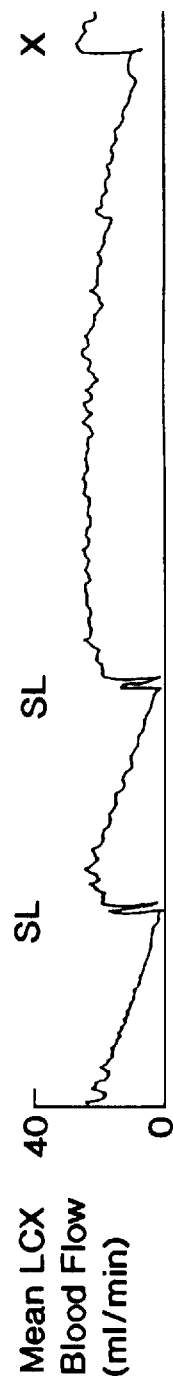

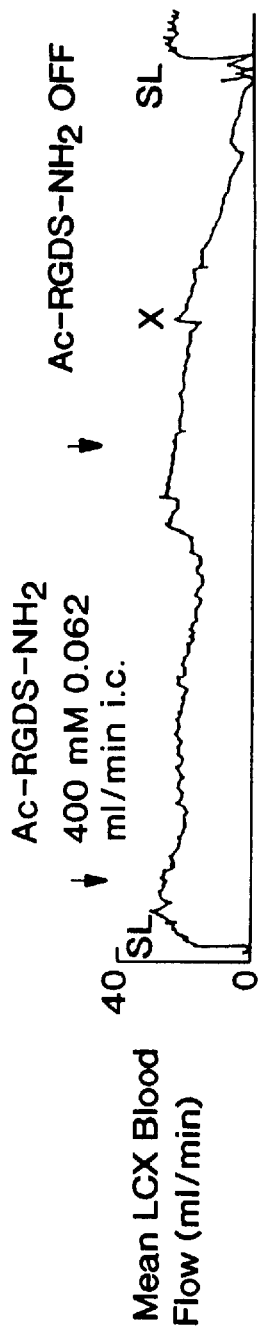
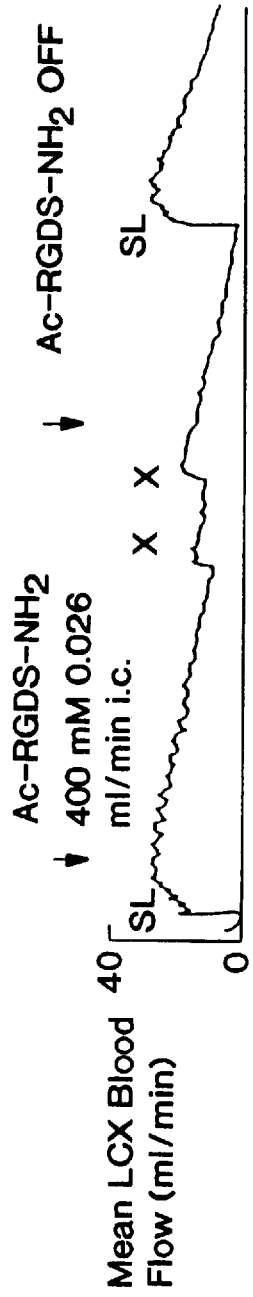
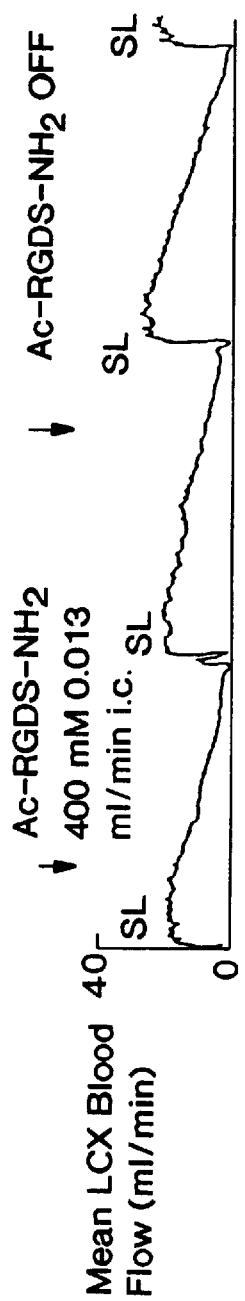
FIG. 3a
FIG. 3b
FIG. 3c

ANTI-AGGREGATORY PEPTIDES

This is a divisional of application Ser. No. 07/335,306 filed on Apr. 10,1989, which is a continuation-in-part of United States Ser. No. 07/191,515, filed May 9, 1988, now abandoned.

FIELD OF THE INVENTION

This invention relates to novel peptides which inhibit platelet aggregation, pharmaceutical compositions containing the peptides and methods of using the peptides. In particular, a method of using the peptides of this invention in combination with fibrinolytic agents is disclosed.

BACKGROUND OF THE INVENTION

A thrombus is the result of processes which initiate the coagulation cascade. It is composed of an aggregation of platelets enmeshed in a polymeric network of fibrin. This process is normally initiated as a consequence of tissue injury and has the effect of slowing or preventing blood flow in a vessel. Etiological factors which are not directly related to tissue injury, such as atherosclerotic plaque, inflammation of the blood vessels (phlebitis) and septicemia, may also initiate thrombus formation. In some instances, the inappropriate formation of a thrombus, and subsequent decrease in blood flow, may have pathological consequences, such as stroke, pulmonary embolism and heart disease.

The coagulation cascade is a multifactorial process which produces as its penultimate step the proteolytic enzyme, thrombin, which hydrolyzes fibrinogen at two specific Arg-Gly residues to form two smaller fibrino-peptides and the fibrin monomer. Two complementary binding sites are exposed by the removal of the fibrino-peptides, and each fibrin monomer can bind to two other monomers to form a polymeric network. Platelets are also activated by thrombin and can bind to fibrinogen and fibrin monomers. These platelets further amplify the process by releasing other activators of coagulation. As this polymerization of fibrin proceeds, the aggregate precipitates from the blood to form the so-called soft clot. Fibrin-stabilizing factor (FSF), which is an enzyme also activated by thrombin, catalyzes the formation of covalent cross-links to form the final hard clot.

Platelets play a major role in thrombus formation. This is mediated primarily through a platelet receptor complex termed GPIIb-IIIa. Von Willebrand factor, a plasma protein, and fibrinogen are able to bind and crosslink GPIIb-IIIa receptors on adjacent platelets and thereby effect aggregation of platelets. Fibronectin, vitronectin and thrombospondin are proteins which have also been demonstrated to bind to GPIIb-IIIa. Fibronectin is found in plasma and as a structural protein in the intracellular matrix. Binding between the structural proteins and GPIIb-IIIa may function to cause platelets to adhere to damaged vessel walls.

Fibronectin and vitronectin are members of a class of structural proteins which promote a broad range of cell attachment functions. Elucidation of the amino acid sequence of the cell attachment domain of some of these proteins, particularly fibronectin, has established the sequence Arg-Gly-Asp (in single letter amino acid code, RGD) as part of the essential structure which mediates binding. See Ruoslahti et al., *Science*, 238, 491–7 (1987). Polypeptides that possess cell attachment properties, prepared from human plasma fibronectin, have been disclosed (Pierschbacher et al., U.S. Pat. No. 4,589,881 (1986) and Rouslahti et al., WO 84/00540 (1984)). Smaller peptides which also contain this sequence have been shown to possess properties of cell adhesion for normal rat kidney (NRK) cells when affixed to a solid support and to inhibit adhesion of these cells to fibronectin when used in solubilized form. See Rouslahti et al., U.S. Pat. No. 4,578,079 (1986) and Rouslahti et al., U.S. Pat. No. 4,614,517 (1986).

Platelet activation is required for binding of GPIIb-IIIa to fibrinogen, fibronectin and von Willebrand factor. Although the exact mechanism is not known, ADP or thrombin stimulation of platelets appears to effect a change in the receptor complex and to facilitate binding. The importance of this receptor to platelet aggregation has been demonstrated by methods which mask the receptor. Thus, Coller et al. (*Blood*, 66, 1456–9 (1985)) have shown that antibodies to this complex inhibit platelet aggregation in dogs induced by ADP. Nievelstein et al. (*Thromb. and Hemostasis*, 58, 2133 (1987)) have reported that -RGDS- peptides inhibit thrombin induced aggregation and adhesion of platelets to fibronectin, and may interact through the GPIIb-IIIa complex. Zimmerman et al., U.S. Pat. No. 4,683,291 (1987) have disclosed peptides containing Arg and Lys and an -RGD- sequence which inhibit binding of fibrinogen to platelets and inhibit platelet aggregation.

Current antithrombotic therapy employs agents that modify the platelet/endothelial cell arachidonate-prostaglandin system, such as prostacyclin analogues, cyclooxygenase inhibitors, thromboxane synthesis inhibitors and thromboxane receptor antagonists; and anticoagulants, such as heparin. These agents inhibit one or both of two discernible phases of platelet aggregation. The primary phase, which is a response to chemical stimuli, such as ADP (adenosine diphosphate), collagen, epinephrine or thrombin, causes initial activation of the platelets. This is followed by a secondary phase, which is initiated by the platelets themselves, and is characterized by thromboxane $A_2$ ($TxA_2$) synthesis and the release of additional ADP from platelet storage granules. These mediators further activate other platelets.

Prostacyclin, also called prostaglandin $I_2(PGI_2)$, is naturally produced by endothelial cells lining the blood vessel walls. $PGI_2$ elevates platelet cAMP, which results in down regulation of the GPIIb-IIIa receptor, thereby inhibiting fibrinogen mediated platelet aggregation and platelet activation in intact blood vessels. $PGI_2$ and stable $PGI_2$ analogues inhibit both the primary and secondary phases of platelet aggregation However, use of such analogues has been associated with undesirable changes in blood pressure. See Aiken, et al., *Prostaglandins*, 19, 629–43 (1980).

Cyclooxygenase is the enzyme responsible for the synthesis of prostaglandins, such as $PGI_2$ and $PGH_2$. PGH2 is further transformed to $TxA_2$ by thromboxane synthase. $TxA_2$ is a powerful activator of platelet aggregation. Cyclooxygenase inhibitors and thromboxane synthetase inhibitors act to block the production of $TxA_2$, while $TxA_2$ antagonists block the effects of $TxA_2$ by binding the $TxA_2$ receptor. All of these therapies act only upon the secondary stage of platelet activation. Cyclooxygenase inhibitors have an additional disadvantage due to their inhibition of synthesis of $PGI_2$, which somewhat obviates the positive anti-aggregatory effects of PGI2 production. Use of cyclooxygenase inhibitors has been associated with ulcerogenesis.

Heparin is a mucopolysaccharide which binds prothrombin, as well as certain other factors in the coagulation cascade. It exerts its effect by preventing the activation of fibrinogen by thrombin and by preventing the activation of the GPIIb-IIIa receptor by thrombin. This inhibits only the primary phase of platelet aggregation and has little effect upon activation of platelets by other means, such as collagen, ADP and epinephrine.

Thus cyclooxygenase inhibitors, prostaglandin analogues and heparin all inhibit platelet aggregation indirectly by inhibiting the primary or secondary phase of platelet/fibrinogen activation. There is therefore a need for selective therapeutic products which block platelet aggregation directly, whether it arises from the primary or secondary phase of platelet activation.

Recent advances for treatment of occluded arteries and deep vein thrombosis employ fibrinolytic agents to lyse thrombi or emboli in order to reestablish or improve blood flow. Fibrinolytic agents are proteolytic enzymes which hydrolyze fibrin at specific sites and thereby fragment the fibrin network. Fragmentation of fibrin into smaller peptides has the effect of solubilizing the thrombus or embolus. Tissue plasminogen activator (tPA), urokinase (UK) and pro-Urokinase(pUK), which are of human origin, and streptokinase (SK), which is of bacterial origin, are considered fibrinolytic agents within the context of this disclosure. Their action in vivo is to proteolytically activate plasminogen in the blood to form plasmin, which is the actual fibrinolytic agent. Of these, tPA and SK are commercially used for fibrinolytic therapy. A recurrent problem with such therapy, however, is the reocclusion of the blood vessel due to formation of a secondary thrombus.

Fibrinolytic therapy is most commonly used for re-establishing flow in a thrombosed blood vessel. It is useful for dissolution of the thrombus which is often the immediate cause of blockage. However, fibrinolytic therapy does not reverse the factors responsible for the initiation of the thrombus. For this reason, anticoagulants such as heparin are often used to prevent reocclusion. In fact, patients which have a high degree of stenosis in an artery are at extremely high risk of rethrombosis after reperfusion, even in the presence of high doses of heparin. See Gold et al., *Circ.*, 73, 347–52 (1986). In addition, use of SK and tPA has been associated with platelet hyperaggregability. See Ohlstein, et al., *Thromb. Res.*, 4, 575–85 (1987). Treatment with higher doses of tPA can be associated with systemic bleeding and is not recommended for preventing reocclusion. There is, therefore, a need for a method for preventing rethrombosis after fibrinolytic therapy.

Recently TxA$_2$ antagonists have shown some promise for inhibiting reocclusion following reperfusion and for lowering the dose of tPA required for fibrinolysis. See EP-A 265 129. Yasuda et al. (*Clin. Res.*, 34, 2 (1986)) have demonstrated that reocclusion by fibrin rich platelet thrombi, after thrombolysis with tPA, may be inhibited by a murine monoclonal antibody to GPIIb-IIIa in dogs.

SUMMARY OF THE INVENTION

It is an object of this invention to provide a method for inhibiting platelet aggregation and the formation of thrombi which employs a peptide or polypeptide which binds to the platelet GPIIb-IIIa receptor. In this manner, the ability of activated platelets to bind von Willebrand's factor, fibronectin and fibrinogen/fibrin is inhibited. This mode of anti-aggregatory activity is unique in that it does not rely merely upon inhibiton of one stimulus of the aggregatory process, but interferes with a final step which is common to all known stimuli. Since other anti-thrombotic/anti-coagulant methods operate by non-analogous means, such peptides or polypeptides will be termed "anti-fibrotics" to distinguish them both mechanistically and structurally from the prior methods.

In one aspect this invention is a compound of the formula (I) or (II):

$$X\text{-}(A)_m\text{-}B\text{-}Gly\text{-}Asp\text{-}(C)_n\text{-}Y \qquad (I)$$

wherein:

A is Arg, HArg, (Me$_2$)Arg, (Et$_2$)Arg, Ala, Gly, His, Abu or an α-R' substituted derivative thereof, or Pro;

B is Arg, HArg, (Me$_2$)Arg, (Et$_2$)Arg or an α-R' substituted derivative thereof;

C is a D or L amino acid chosen from Tyr, (Alk)Tyr, Phe, (4'W)Phe, HPhe, Phg, Trp, His, Ser, (Alk)Ser, Thr, (Alk)Thr, Cys, (Alk)Cys, Pen, (Alk)Pen, Ala, Val, Nva, Met, Leu, Ile, Nle or Nal;

W is halogen or Alk;

Y is NR$_1$R$_2$ or OR$_3$;

R$_1$ and R$_2$ are each independently H, Alk or (CH$_2$)$_p$Ph;

R$_3$ is Alk, (CH$_2$)$_p$Ph or, when B is HArg, (Me$_2$)Arg, (Et$_2$)Arg, or an α-R' substituted derivative of Arg, HArg, (Me$_2$)Arg or (Et$_2$)Arg, H;

X is R$_4$R$_5$N;

R$_4$ is H or Alk;

R$_5$ is H, Alk, HCO, AlkCO, PhCH$_2$ or PH(CH 2)$_q$CO;

R' is Alk or PhCH$_2$;

q, m and n are 0 or 1; and p is 0, 1, 2 or 3;

or a pharmaceutically acceptable salt thereof; or

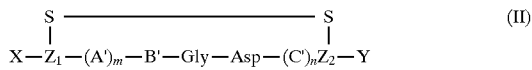
$$\text{(II)}$$

wherein:

A' is a D- or L-amino acid chosen from Arg, HArg, (Me$_2$)Arg, (Et$_2$)Arg, Ala, Gly, His, Abu, Lys or an α-R' substituted derivative thereof, or Pro;

B' is a D- or L-amino acid chosen from Arg, HArg, (Me$_2$)Arg, (Et$_2$)Arg, Lys or an α-R' substituted derivative thereof;

C' is a D or L amino acid chosen from Tyr, (Alk)Tyr, Phe, (4'W)Phe, HPhe, Phg, Trp, His, Ser, (Alk)Ser, Thr, (Alk)Thr, (Alk)Cys, (Alk)Pen, Ala, Val, Nva, Met, Leu, Ile, Nle or Nal, or an α-R' substituted derivative hereof;

W is halogen or Alk;

Y is NR$_1$R$_2$ or OR$_3$;

R$_1$ and R$_2$ are each independently H, Alk or (CH$_2$)$_p$Ph;

R$_3$ is Alk, (CH$_2$)$_p$Ph or, when B is HArg, (Me$_2$)Arg, (Et$_2$)Arg, or an α-R' substituted derivative of Arg, HArg, (Me$_2$)Arg or (Et$_2$)Arg, H;

X is R$_4$R$_5$N or H;

R$_4$ is H or Alk;

R$_5$ is H, Alk, HCO, AlkCO, PhCH$_2$ or Ph(CH$_2$)$_q$CO;

R' is Alk or PhCH$_2$;

Z$_1$ is a D- or L-isomer of Cys, Pen or APmp;

Z$_2$ is a D- or L-isomer of Cys, Pen or APmp;

q, m and n are independently 0 or 1; and p is 0, 1, 2 or 3;

or a pharmaceutically acceptable salt thereof.

This invention is also a pharmaceutical composition for inhibiting platelet aggregation and clot formation, which comprises an anti-fibrotic peptide and a pharmaceutically acceptable carrier.

This invention is further a method for treating thrombosis or embolism, or for inhibiting platelet aggregation or clot formation in a mammal in need thereof, which comprises internally administering an effective amount of an anti-fibrotic peptide of formula (I) or (II).

The compounds of this invention, as well as others which may operate through the same mechanism, are also particularly useful for prevention of rethrombosis during thrombolytic therapy. Therefore, in another aspect, it is an object of this invention to provide a method for inhibiting reocclusion of an artery or vein in a mammal following thrombolysis, which comprises internally administering an effective amount of a fibrinolytic agent and an anti-fibrotic peptide. In combination with known fibrinolytics, such as streptokinase (SK), urokinase (UK), pro-urokinase (pUK) and tissue plasminogen activator (tPA) and variants or mutants thereof, the peptides described above are useful for inhibiting rethrombosis. In addition, certain other peptides and polypeptides, which contain the amino acid sequence -RGD-, are useful in this invention, especially certain fragments or derivatives of von Willebrands factor, human plasma fibrinogen and human plasma fibronectin.

This invention may also be embodied as a pharmaceutical composition for effecting thrombolysis and reperfusion, and inhibiting reocclusion in an artery or vein in a mammal, which comprises a fibrinolytic and an anti-fibrotic peptide in a pharmaceutical carrier.

Finally, this invention is a kit for use in a method for effecting thrombolytic therapy, which comprises, in one container, a fibrinolytic and, in a second container, an anti-fibrotic peptide.

A BRIEF DESCRIPTION OF THE FIGURES

FIG. 1 demonstrates that the peptide Ac-RGDS-NH$_2$ has no effect upon tPA promoted human clot lysis in vitro. The graph displays the % clot lysis at 4 hours as a function of increasing concentrations of tissue plasminogen activator (tPA). The squares represent tPA(MT2N3)-induced lysis in the control period (EC$_{50}$=31.5±9.9 μg/ml) and the circles represent lysis in the presence of tPA and 1 mM Ac-RGDS-NH$_2$ (EC$_{50}$=31.9±8.6 μg/ml).

FIG. 2 demonstrates the inhibition of platelet aggregation in vivo by infusion of 400 mM Ac-RGDS-NH$_2$ at a rate of 0.1 ml/min. Platelet aggregation/thrombus formation is indicated by a reduction in blood flow. Arrows indicate initiation and termination of infusion. SL (shake loose) indicates mechanical dislodgement of the thrombus. Top trace (a) displays the coronary arterial blood pressure (mmHg) as a function of time, which indicates no effect of infusion of Ac-RGDS-NH$_2$ upon blood pressure. Middle trace (b) demonstrates the variation of phasic coronary blood flow (ml/min) as a function of time, which indicates inhibition of thrombus formation after infusion of the peptide. Lower trace (c) displays the mean coronary blood flow (ml/min) as a function of time, which indicates inhibition of thrombus formation after infusion of the peptide.

FIGS. 3A–3C demonstrate the dose dependency of in vivo inhibition of platelet aggregation in the coronary thrombosis model. The graph displays mean coronary blood flow as a function of time. Arrows indicate the initiation and termination of infusion of Ac-RGDS-NH$_2$. Thrombus formation is indicated by a decrease in blood flow. SL (shake loose) indicates a mechanical dislodgement of a thrombus, X indicates spontaneous sloughing off of a thrombus. The top trace (a) indicates complete inhibition of thrombus formation (400 mM at 0.052 ml/min. infusion rate). The middle trace (b) indicates moderate inhibition with spontaneous sloughing off of thrombi (400 mM at 0.026 ml/min. infusion). The bottom trace (c) shows partial inhibition with prolongation of time to complete blockage, requiring mechanical dislodgement of thrombus (400 mM at 0.013 ml/min.).

DETAILED DESCRIPTION OF THE INVENTION

Figure 1:
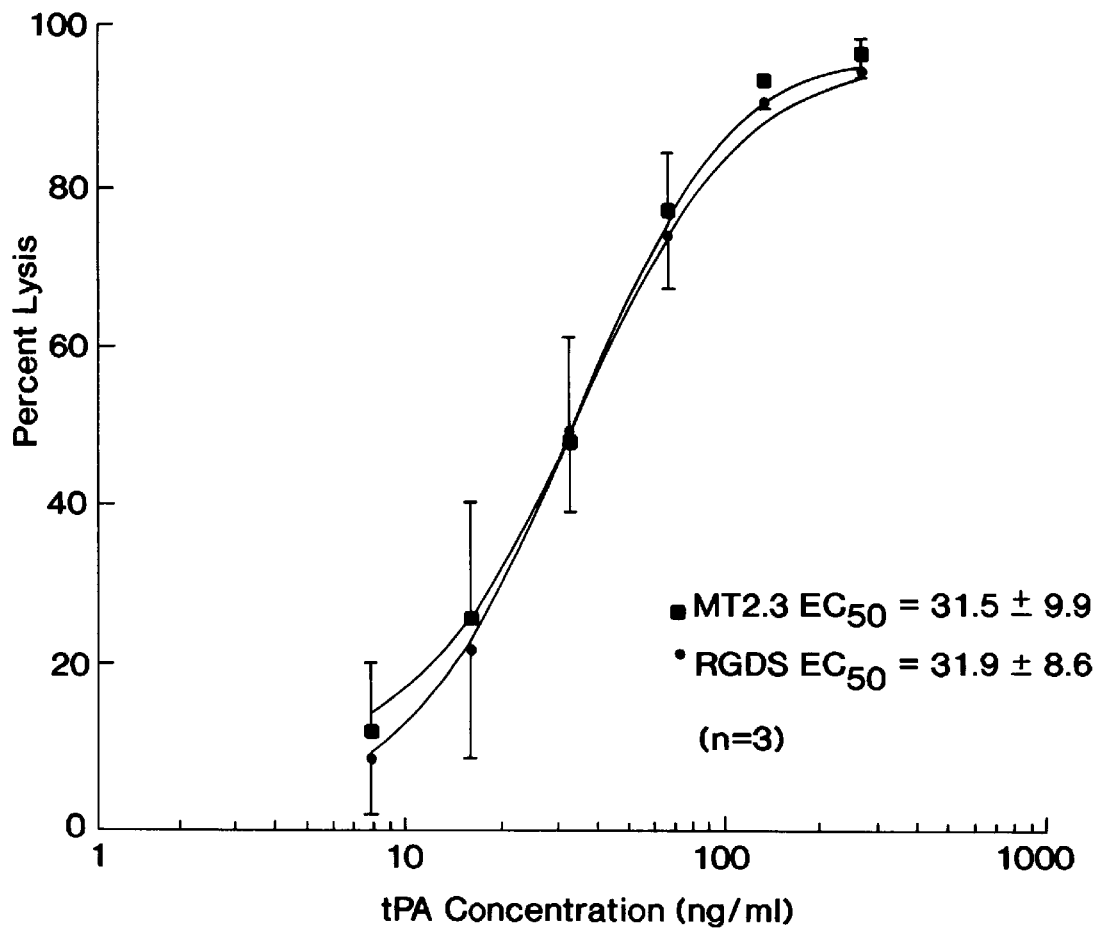

It has been found that certain peptides inhibit the aggregation of platelets. Such peptides are believed to interact with receptors on platelets, typified by the GPIIb-IIIa complex, which are able to bind a wide range of endogenous structural proteins, such as fibronectin and vitronectin. Thus, injury, disruption or irregularity of the intima of a blood vessel exposes the underlying structural proteins of the extracellular matrix, and platelets can be demonstrated to bind to the vessel wall presumably through the GPIIb-IIIa receptor. In addition, fibrinogen/fibrin and von Willebrand factor have been shown to interact with the GPIIb-IIIa receptor complex on platelets. This promotes the aggregation of platelets via the multivalent binding of the GPIIb-IIIa receptor. Interference of these adhesive interactions between the platelet receptor and fibrinogen, von Willebrands factor, and fibronectin may be effected by mimicking the binding site of these proteins. Analysis of an active fragment of fibronectin has shown the binding site of fibronectin to contain the amino acid sequence Arg-Gly-Asp (RGD). It has further been shown that peptides containing this sequence are able to inhibit attachment of cells to fibronectin and to inhibit the binding of von Willebrands factor and fibrinogen to platelets. Thus certain proteins, naturally occurring polypeptide fragments and derivatives of these fragments are able to inhibit platelet aggregation. F(ab')$_2$ fragments of a monoclonal antibody (Coller et al., *Blood*, 66, 1456–9 (1985)) and peptide fragments of human plasma fibronectin (Rouslahti et al., PCT WO 84/00540 (1984) and Pierschbacher, et al., U.S. Pat. No. 4,589,881 (1986)) are capable of binding the GPIIb-IIIa receptor.

This invention discloses peptides comprising the sequence Gly-Asp which may bind the platelet GPIIb-IIIa receptor, and thereby inhibit platelet aggregation. One aspect of this invention is to modify the conformation of the RGD sequence by proper choice of adjoining amino acids and derivatization or replacement of the Arg within this sequence in order to facilitate the binding of peptides to platelets. Another aspect of this invention is the protection of the amino terminus of the peptide by acetylation or alkylation, and the modification of the carboxyl terminus as an amide, substituted amide or ester. These modifications enhance stability of the peptide to proteolytic enzymes and distinguishes them from compounds which have been used previously to promote cell adhesion (Rouslahti et al., U.S. Pat. No. 4,578,079 (1986) and Rouslahti et al., U.S. Pat. No. 4,614,517 (1986)) and to inhibit platelet aggregation (Zimmerman et al., U.S. Pat. No. 4,683,291 (1987)). Certain of the peptides of this invention contain an intramolecular disulfide bond which enhances both their metabolic stability and biological activity.

The compounds of this invention are tri-, tetra-, penta-, hexa- and heptapeptides of the formula (I) and (II):

$$X-(A)_m-B-Gly-Asp-(C)_n-Y \qquad (I)$$

wherein:

A is Arg, HArg, (Me$_2$)Arg, (Et$_2$)Arg, Ala, Gly, His, Abu or an α-R' substituted derivative thereof, or Pro;

B is Arg, HArg, (Me$_2$)Arg, (Et$_2$)Arg or an α-R' substituted derivative thereof;

C is a D or L amino acid chosen from Tyr, (Alk)Tyr, Phe, (4'W)Phe, HPhe, Phg, Trp, His, Ser, (Alk)Ser, Thr, (Alk)Thr, Cys, (Alk)Cys, Pen, (Alk)Pen, Ala, Val, Nva, Met, Leu, Ile, Nle or Nal;

W is halogen or Alk;
Y is $NR_1R_2$ or $OR_3$;
$R_1$ and $R_2$ are each independently H, Alk or $(CH_2)_pPh$;
$R_3$ is Alk, $(CH_2)_pPh$ or, when B is HArg, $(Me_2)Arg$, $(Et_2)Arg$, or an α-R' substituted derivative of Arg, HArg, $(Me_2)Arg$ or $(Et_2)Arg$, H;
X is $R_4 R_5N$;
$R_4$ is H or Alk;
$R_5$ is H, Alk, HCO, AlkCO, $PhCH_2$ or $Ph(CH_2)_qCO$;
R' is Alk or $PhCH_2$;
q, m and n are 0 or 1; and
p is 0, 1, 2 or 3;
or a pharmaceutically acceptable salt thereof.

Suitably A is Gly or Arg, and when m is 1, n is suitably 0.

B is suitably HArg or an α-R' substituted derivative of Arg or HArg. B is preferably MeArg.

C is suitably Ser, (Me)Ser, Thr, Tyr, Phe, Val or Nal. When n is 1, m is suitably 0.

The compounds of this invention are also penta-, hexa- or heptapeptides of formula (II):

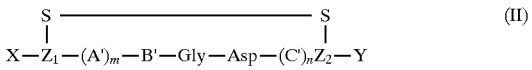

$$X-Z_1-(A')_m-B'-Gly-Asp-(C')_nZ_2-Y \quad (II)$$

wherein:
A' is a D- or L-amino acid chosen from Arg, HArg, $(Me_2)Arg$, $(Et_2)Arg$, Ala, Gly, His, Abu, Lys or an α-R' substituted derivative thereof, or Pro;
B' is a D- or L-amino acid chosen from Arg, HArg, $(Me_2)Arg$, $(Et_2)Arg$, Lys or an α-R' substituted derivative thereof;
C' is a D or L amino acid chosen from Tyr, (Alk)Tyr, Phe, (4'W)Phe, HPhe, Phg, Trp, His, Ser, (Alk)Ser, Thr, (Alk)Thr, (Alk)Cys, (Alk)Pen, Ala, Val, Nva, Met, Leu, Ile, Nle or Nal, or an α-R' substituted derivative thereof;
W is halogen or Alk;
Y is $NR_1R_2$ or $OR_3$;
$R_1$ and $R_2$ are each independently H, Alk or $(CH_2)_pPh$;
$R_3$ is Alk, $(CH_2)_pPh$ or, when B' is HArg, $(Me_2)Arg$, $(Et_2)Arg$, or an α-R' substituted derivative of Arg, HArg, $(Me_2)Arg$ or $(Et_2)Arg$, H;
X is $R_4R_5N$ or H;
$R_4$ is H or Alk;
$R_5$ is H, Alk, HCO, AlkCO, $PhCH_2$ or $Ph(CH_2)_qCO$;
R' is Alk or $PhCH_2$;
$Z_1$ is a D- or L-isomer of Cys, Pen or APmp;
$Z_2$ is a D- or L-isomer of Cys, Pen or APmp;
q, m and n are independently 0 or 1; and
p is 0, 1, 2 or 3;
or a pharmaceutically acceptable salt thereof.

Suitably, A' is Gly or Arg, and when m is 1, n is preferably 0.

B' is suitably HArg or an α-R' substituted derivative of Arg or HArg. B is preferably MeArg.

C' is suitably Ser, (Me)Ser, Thr, Tyr, Phe or Nal. When n is 1, m is suitably 0.

$Z_2$ is preferably an L-isomer of APmp, Cys or Pen.

Preferably both m and n are 0.

The meaning of X in the formulae herein depicted is intended to denote the amino terminus of the peptide and thereby departs from convention. It should be apparent that when X is H, $Z_1$ is a desamino acid. For example, when $Z_1$ is Cys and X is H, the residue corresponds to des-amino cysteine, which is 3-mercaptopropanoic acid (Mpa).

Specific compounds of this invention are:
$N^α$-Ac-Cyclo(S,S) Cys-MeArg-Gly-Asp-Ser-Cys-$NH_2$;
$N^α$-Ac-Cyclo(S,S) Cys-Arg-Gly-Asp-(D,L) APmp-$NH_2$;
$N^α$-Ac-Cyclo(S,S) Cys-Arg-Gly-Asp-Ser-Cys-$NH_2$;
Cyclo(S,S)Mpr-Arg-Gly-Asp-Ser-Cys-$NH_2$;
$N^α$-Ac-Cyclo(S,S)Cys-MeArg-Gly-Asp-Ser-Pen-$NH_2$;
$N^α$-Ac-Cyclo(S,S) Cys-MeArg-Gly-Asp-(Me)Ser-Cys-$NH_2$;
Cyclo(S,S)Mpr-MeArg-Gly-Asp-Ser-Cys-$NH_2$;
$N^α$-Ac-Cyclo(S,S)Cys-MeArg-Gly-Asp-Cys-$NH_2$;
Cyclo(S,S)Mpr-MeArg-Gly-Asp-Pen-$NH_2$;
$N^α$-Ac-Cyclo(S,S)Cys-Arg-Gly-Asp-Pen-$NH_2$;
$N^α$-Ac-Cyclo(S,S)Cys-Arg-Gly-Asp-D-Pen-$NH_2$;
$N^α$-Ac-Cyclo(S,S)Cys-Lys-Gly-Asp-Pen-$NH_2$;
$N^α$-Ac-Cyclo(S,S)Cys-HArg-Gly-Asp-Pen-$NH_2$;
$N^α$-Ac-Cyclo(S,S)Cys-MeArg-Gly-Asp-Pen-$NH_2$;
$N^α$-Ac-Cyclo(S,S)Cys-Arg-Gly-Asp-Pen-NHET
$N^α$-Ac-Cyclo(S,S)Cys-D-Arg-Gly-Asp-Pen-$NH_2$;
$N^α$-Ac-Cyclo(S,S)Cys-MeArg-Gly-Asp-Tyr-Cys-$NH_2$;
$N^α$-Ac-Cyclo(S,S)Pen-MeArg-Gly-Asp-Pen-$NH_2$;
$N^α$-Ac-Cyclo(S,S)Pen-Arg-Gly-Asp-Cys-$NH_2$;
$N^α$-Ac-Cyclo(S,S)Cys-D-Arg-Gly-Asp-Ser-Cys-$NH_2$;
$N^α$-Ac-Cyclo(S,S)Cys-Sar-Arg-Gly-Asp-Pen-$NH_2$;
$N^α$-Ac-Cyclo(S,S)Cys-Arg-Gly-Asp-Cys-$NH_2$;
$N^α$-Ac-Cyclo(S,S)Cys-Arg($Et_2$)-Gly-Asp-Pen-$NH_2$;
$N^α$-Ac-Cyclo(S,S)Cys-D-MeArg-Gly-Asp-Pen-$NH_2$;
$N^α$-Ac-MeArg-Gly-Asp-Ser-$NH_2$;
$N^α$-Ac-Arg-Gly-Asp-Ser-$NH_2$;
$N^α$-Ac-Arg-Gly-Asp-Tyr-$NH_2$;
$N^α$-Ac-Arg-Gly-Asp-$NH_2$;
$N^α$-Ac-Arg-Gly-Asp-D-Ser-$NH_2$;
$N^α$-Ac-Arg-Gly-Asp-Val-$NH_2$;
$N^α$-Ac-Arg-Gly-Asp-Nal-$NH_2$;
$N^α$-Ac-Arg-Arg-Gly-Asp-Phe-$NH_2$;
$N^α$-Ac-Arg-Gly-Asp-NH-$CH_2$-$CH_2$-$C_6H_5$
$N^α$-Ac-MeArg-Gly-Asp-Phe-$NH_2$;
$N^α$-Ac-HArg-Gly-Asp-Ser-$NH_2$;
$N^α$-Ac-Arg-Gly-Asp-Ser-NHEt;
$N^α$-MeArg-Gly-Asp-Ser-$NH_2$;
$N^α$-Formyl-MeArg-Gly-Asp-Ser-$NH_2$; or
Gly-MeArg-Gly-Asp-Ser-$NH_2$;

The nomenclature commonly used in the art is used herein to describe the peptides.

| Amino acid | Three-letter symbol | One-letter symbol | Amino acid | Three-letter symbol | One-letter symbol |
|---|---|---|---|---|---|
| Alanine | Ala | A | Isoleucine | Ile | I |
| Arginine | Arg | R | Leucine | Leu | L |
| Asparagine | Asn | N | Lysine | Lys | K |
| Aspartic acid | Asp | D | Methionine | Met | M |
| Asn and/or Asp | Asx | B | Phenylalanine | Phe | F |

| Amino acid | Three-letter symbol | One-letter symbol | Amino acid | Three-letter symbol | One-letter symbol |
|---|---|---|---|---|---|
| Cysteine | Cys | C | Proline | Pro | P |
| Glutamine | Gln | Q | Serine | Ser | S |
| Glutamic acid | Glu | E | Threonine | Thr | T |
| Gln and/or Glu | Glx | Z | Tryptophan | Trp | W |
| Glycine | Gly | G | Tyrosine | Tyr | Y |
| Histidine | His | H | Valine | Val | V |

In accordance with conventional representation, the amino terminus is on the left and the carboxy terminus is on the right. Unless specified otherwise, all chiral amino acids (AA) are assumed to be of the L-absolute configuration. Pen refers to L-penicillamine or β,β dimethyl cysteine, APmp refers to 2-amino-3,3-cyclopentamethylene-3-mercaptopropionic acid, Mpa refers to 3-mercaptopropionic acid, Pmp refers to 3,3-cyclopentamethylene-3-mercaptopropionic acid, Mdp refers to 3-mercapto-3-methylbutanoic acid, HArg refers to homoarginine, $(Me_2)$Arg refers to N', N''-dimethyl arginine, $(Et_2)$Arg refers to N', N''-diethyl arginine, Nva refers to norvaline, Nle refers to norleucine, α-MeAsp refers to $N^\alpha$-methyl aspartic acid, Nal refers to beta-2-napthyl alanine, Phg refers to phenyl glycine, HPhe refers to homophenylalanine, Trp refers to tryptophan, Abu refers to 2-amino butyric acid, (Alk)Tyr refers to O-$C_{1-4}$alkyl-tyrosine, (Alk)Ser refers to O-$C_{1-4}$ alkyl-serine, (Alk)Thr refers to O-$C_{1-4}$ alkyl-threonine, (Alk)Cys refers to S-$C_{1-4}$ alkyl-cysteine, (Alk)Pen refers to S-$C_{1-4}$ alkyl-penicillamine, (4'W)Phe refers to phenylalanine substituted in the 4 position of the phenyl ring by W, Boc refers to the t-butyloxycarbonyl radical, Fmoc refers to the fluorenylmethoxycarbonyl radical, Ph refers to the phenyl radical, Cbz refers to the carbobenzyloxy radical, BrZ refers to the o-bromobenzyloxycarbonyl radical, Clz refers to the o-chlorobenzyloxycarbonyl radical, Bzl refers to the benyzl radical, 4-MBzl refers to the 4-methyl benzyl radical, Ac refers to acetyl, Alk refers to $C_{1-4}$ alkyl, Ph refers to phenyl, Chx refers to cyclohexyl, DCC refers to dicyclohexylcarbodiimide, DMAP refers to dimethylaminopyridine, HOBT refers to 1-hydroxybenzotriazole, THF refers to tetrahydrofuran, DMF refers to dimethyl formamide, HF refers to hydrofluoric acid and TFA refers to trifluoroacetic acid. $C_{1-4}$ alkyl as applied herein is meant to include methyl, ethyl, propyl, isopropyl, butyl and isobutyl.

α-R' substituted derivatives of the amino acids of this invention, which may be denoted as (α-R')AA, indicate amino acids which are mono-substituted on the α-amino group by R', wherein R' is Alk or benzyl. R' is preferably methyl. $N^\alpha$-methyl arginine and $N^\alpha$-methyl glycine, which are (α-Me)Arg and (α-Me)Gly respectively, are also denoted herein as MeArg and Sar (sarcosine) in accordance with past conventional notation. All other N-α-substituted amino acids will carry the designation α- in their representation. Thus, amino acids which may be alkylated upon a mercaptan, guanidino or hydroxyl group, such as Tyr, Ser, Thr, Cys or Pen, are distinguished by an absence of this designation. Thus, (α-Me)Ser is $N^\alpha$-methyl serine, (Me)Ser is O-methyl serine, (α-Me, Et)Ser is $N^\alpha$-methyl, O-ethyl serine and (α-Me, $Et_2$)Arg is $N^\alpha$-methyl-N',N''-diethyl arginine.

The peptides are prepared preferably by the solid phase technique of Merrifield (J. Am. Chem. Soc., 85, 2149 (1964)), although solution methods known to the art may be successfully employed. A combination of solid phase and solution synthesis may be used, as in a convergent synthesis in which di-, tri-, tetra-, or penta-peptide fragments may be prepared by solid phase synthesis and either coupled or further modified by solution synthesis. The methods of peptide synthesis generally set forth by Ali et al. in *J. Med. Chem.*, 29, 984 (1986) and *J. Med. Chem.*, 30, 2291 (1987) were employed to produce most of the peptides of this invention and are incorporated herein by reference.

Each amino acid or peptide is suitably protected as known in the peptide art. For example, the Boc, Cbz or Fmoc group may be used for protection of an amino group, especially an α-amino group. The Boc group is generally preferred for protection of the α-amino group. A benzyl group or suitably substituted benzyl group is used to protect the mercapto group of cysteine, or other thiol containing amino acids; or the hydroxyl of serine or threonine. The tosyl group may be used for protection of the imidazolyl group of His, and tosyl or nitro group for protection of the guanidino nitrogen of Arg. A suitably substituted carbobenzyloxy group or benzyl group may be used for the hydroxyl group of Tyr, Ser or Thr, or the ε-amino group of lysine. The phthalamido group may also be used for the protection of the ε-amino group of lysine. Suitable substitution of the carbobenzyloxy or benzyl protecting groups is ortho and/or para substitution with chloro, bromo, nitro or methyl, and is used to modify the reactivity of the protective group. Cysteine and other sulfur-containing amino acids may also be protected by formation of a disulfide with a thioalkyl or thioaryl group. Except for the Boc group, the protective groups are, most conveniently, those which are not removed by mild acid treatment. These protective groups are removed by such methods as catalytic hydrogenation, sodium in liquid ammonia or HF treatment as known in the art.

If solid phase methods are used, the peptide is built up sequentially starting from the carboxy terminus and working toward the amino terminus of the peptide. Solid phase synthesis is begun by covalently attaching the C terminus of a protected amino acid to a suitable resin, such as a benzhydrylamine resin (BHA), Methylbenzhydrylamine resin (MBHA) or chloromethyl resin (CMR), as is generally set forth in U.S. Pat. No. 4,244,946. A BHA or MBHA support resin is used if the carboxy terminus of the product peptide is to be a carboxamide. A CMR support is generally used if the carboxy terminus of the product peptide is to be a carboxyl group, although this may also be used to produce a carboxamide or ester.

Once the first protected amino acid (AA) has been coupled to the desired resin, the amino group is hydrolyzed by mild acid treatment, and the free carboxyl of the second protected AA is coupled to this amino group. This process is carried out sequentially, without isolation of the intermediate, until the desired peptide has been formed. The completed peptide may then be deblocked and/or split from the carrying resin in any order.

Treatment of a CMR supported peptide with alkali in aqueous alcohol splits the peptide from the resin and produces the carboxy terminal amino acid as a carboxylic acid. Treatment of a CMR supported peptide with ammonia or alkyl amines in an alcoholic solvent provides a carboxamide or alkyl carboxamide at the carboxy terminus.

If an ester is desired, the CMR resin may be treated with an appropriate alcohol, such as methyl, ethyl, propyl, butyl or benzyl alcohol, in the presence of triethylamine to cleave the peptide from the resin and produce the ester directly.

Esters of the peptides of this invention may also be prepared by conventional methods from the carboxylic acid precursor. Typically, the carboxylic acid is treated with an alcohol in the presence of an acid catalyst. Alternatively, the carboxylic acid may be converted to an activated acyl intermediate, such as an acid halide, and treated with an alcohol, preferably in the presence of a base.

Methods of producing C-terminal esters of the peptides without esterification of the side chain carboxyl group of aspartic acid are slightly more elaborate, but are well known to those skilled in the art of peptide synthesis. For example, the synthesis is begun with an ester of the C terminal amino acid, or of a dipeptide, and coupled via solution phase synthesis to an appropriately side-chain-protected aspartic acid residue. The side chain carboxyl group is then selectively deprotected and coupled to a chloromethyl resin (CMR). The amino group is liberated and solid phase peptide synthesis is employed. Subsequent cleavage from the resin, using HF, produces the desired side chain carboxylic acid, whilst the carboxy terminus of the peptide remains as an ester. In a similar manner, if one begins the synthetic sequence with the alkyl amide of an appropriately protected amino acid or dipeptide, one obtains the corresponding C-terminal alkyl amide of the peptide.

For producing esters and substituted amides in such a process, suitable protecting groups for the 4-carboxyl group of aspartic acid are benzyl esters and halogen or alkyl-substituted benzyl esters. When the amino group is protected by the Boc group, the benzyl ester protecting group may be selectively removed by hydrogenation and coupled to a CMR support.

If there are benzyl or substituted benzyl protecting groups (such as for the hydroxyl, thiol or amino group) on the amino acid (or dipeptide) which is to be coupled to the aspartic acid prior to attachment to the resin, a t-butyl ester or other acid labile group is suitable for protecting the side-chain carboxyl of the aspartic acid. In this case the amino group of the aspartic acid is protected by a base labile group, such as the Fluorenylmethoxycarbonyl moiety (Fmoc). After solution phase coupling of the aspartic acid to an amino acid (or dipeptide), selective deprotection of the t-butyl ester is accomplished by mild acid hydrolysis and the side chain carboxyl is coupled to the resin by conventional methods. The fluorenylmethoxycarbonyl group is then removed by mild base for subsequent solid phase peptide synthesis.

The preferred method for cleaving a peptide from the support resin is to treat the resin supported peptide with anhydrous HF in the presence of a suitable cation scavenger, such as anisole or dimethoxy benzene. This method simultaneously removes all protecting groups, except a thioalkyl group protecting sulfur, and splits the peptide from the resin. Peptides hydrolyzed in this way from the CMR are carboxylic acids, those split from the BHA resin are obtained as carboxamides.

Modification of the terminal amino group of the peptide is accomplished by alkylation or acetylation as is generally known in the art. These modifications may be carried out upon the amino acid prior to incorporation into the peptide, or upon the peptide after it has been synthesized and the terminal amino group liberated, but before the protecting groups have been removed.

Typically, acetylation is carried out upon the free amino group using the acyl halide, or anhydride, of the corresponding alkyl acid, in the presence of a tertiary amine. Monoalkylation is carried out most conveniently by reductive alkylation of the amino group with an appropriate aliphatic aldehyde or ketone in the presence of a mild reducing agent, such as lithium or sodium cyanoborohydride. Dialkylation may be carried by treating the amino group with an excess of an alkyl halide in the presence of a base.

Solution synthesis of peptides is accomplished using conventional methods used to form amide bonds. Typically, a protected Boc-amino acid which has a free carboxyl group is coupled to a protected amino acid which has a free amino group using a suitable carbodiimide coupling agent, such as N, N' dicyclohexyl carbodiimide (DCC), optionally in the presence of catalysts such as 1-hydroxybenzotriazole (HOBT) and dimethylamino pyridine (DMAP). Other methods, such as the formation of activated esters, anhydrides or acid halides, of the free carboxyl of a protected Boc-amino acid, and subsequent reaction with the free amine of a protected amino acid, optionally in the presence of a base, are also suitable. For example, a protected Boc-amino acid or peptide is treated in an anhydrous solvent, such as methylene chloride or tetrahydrofuran (THF), in the presence of a base, such as N-methyl morpholine, DMAP or a trialkyl amine, with isobutyl chloroformate to form the "activated anhydride", which is subsequently reacted with the free amine of a second protected amino acid or peptide. The peptide formed by these methods may be deprotected selectively, using conventional techniques, at the amino or carboxy terminus and coupled to other peptides or amino acids using similar techniques.

The α-R' substituted derivatives of the amino acids of this invention, which includes derivatives of Arg, HArg, (Me$_2$) Arg, (Et$_2$)Arg, Ala, Gly, His, Abu, Tyr, (Alk)Tyr, Phe, (4'W)Phe, HPhe, Phg, Trp, His, Ser, (Alk)Ser, Thr, (Alk)Thr, Cys, (Alk)Cys, Pen, (Alk)Pen, Ala, Val, Nva, Met, Leu, Ile, Nle and Nal, are prepared by methods common to the chemical art. The R' sustituent may be Alk, as hereinbefore defined, or benzyl. Representative methods for preparing these derivatives are disclosed in U.S. Pat. No. 4,687,758; Cheung et al., Can. J. Chem., 55, 906 (1977); Freidinger et al., J. Org. Chem., 48, 77, (1982); and Shuman et al., Peptides: Proceedings of the 7th American Peptide Symposium, Rich, D., Gross, E., Eds, Pierce Chemical Co., Rockford, Ill.,617 (1981), which are incorporated herein by reference. Typically, a solution of the Cbz- or Boc-amino acid in DMF/THF is condensed with an appropriate alkyl halide, such as methyl or ethyl iodide, in the presence of a base, such as sodium hydride or potassium hydride. Optionally, a crown ether, such as 18-crown-6 with potassium hydride, may be added to facilitate the reaction. Generally, in this processs and those that follow, if the amino acid bears a functional group such as a hydroxyl, mercaptan, amino, guanidino, indolyl or imidazolyl group, these groups are protected as hereinbefore described. Thus, Boc-Tyr(Bzl) is treated with sodium hydride and methyl iodide in THF/DMF solution at 0° C. and stirred at room temperature for 24 hrs. to yield Boc-(α-Me)Tyr(Bzl).

Alternately, the free amine of the amino acid is reacted with an appropriate aldehyde, such as acetaldehyde or benzaldehyde, in the presence of a reducing agent, such as sodium cyanoborohydride, to effect mono-alkylation. This process is especially useful for preparing α-benzyl amino acids. α-Benzylated amino acids may also be used as intermediates to prepare α-methyl amino acids. For example, α-methyl arginine is prepared in three steps by 1.) reacting Arg(Tos) with benzaldehyde and sodium cyanoborohydride in a methanol solution to yield (α-Bzl) Arg(Tos); 2.) reducing the benzylated product with formaldehyde/formic acid solution to yield (α-Bzl, α-Me) Arg(Tos); and 3.) liberating the benzyl group by catalytic hydrogenation (5% Pd/C in glacial acetic acid/HCl) to yield MeArg(Tos).

α-R' substituted derivatives of amino acids may also be prepared by reduction of oxazolidinones prepared from the Fmoc- or Cbz-amino acids. Typically, an Fmoc- or Cbz-amino acid is heated with an appropriate aldehyde such as acetaldehyde or benzaldehyde, in the presence of toluenesulfonic acid, in toluene solution to produce a 2-substituted 5-oxo-oxazolidine. Reduction of this oxazolidinone with triethylsilane and TFA in chloroform solution affords the Cbz- or Fmoc-α substituted amino acid directly. It will be appreciated by those skilled in the art that when formaldehyde is used, the oxazolidinone is unsubstituted in the 2-position and a-methyl amino acids are produced.

A preferred group of compounds of this invention are those depicted by formula (II). These compounds possess two amino acids which possess thiol groups which are joined in a disulfide bond to form a cyclic structure. Such a structure is produced from the corresponding linear

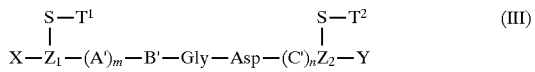

(III)

peptide (III), wherein A', B', Asp, C', $Z_1$, $Z_2$, m, n, p, q, W, X, Y, R', $R_1$, $R_2$, $R_3$, $R_4$, and $R_5$ are as defined hereinbefore, with any chemically reactive centers optionally protected as previously described. $T^1$ and $T^2$ are displaceable groups such as a thioalkyl, thioaryl group, substituted benzyl group or hydrogen. Examples of suitable displaceable groups are hydrogen, thioethyl, benzyl and the 4-methyl benzyl group.

Formation of the disulfide bond may be accomplished by either one of two general methods. If the sulfur-containing amino acids of the linear peptide are protected differently, in such a manner as to allow formation of a mono mercaptan, cyclization may be effected by base catalyzed nucleophilic displacement of the protecting group of the second sulfur-containing amino acid. Groups which are especially useful as displaceable protecting groups are thioalkyl or thioaryl groups. Exemplary of this method is the protection of one sulfur-containing amino acid by the thioethyl group, and protection of the second by a substituted benzyl group. Deprotection of such a peptide by HF removes the benzyl group from one amino acid, while leaving the second protected as an ethyl disulfide. Stirring this mercapto/disulfide in dilute solution at a pH of about 7 to 8 effects displacement of the thioethyl group and cyclization of the linear peptide.

If the corresponding linear peptide of formula (III) is completely deprotected and produced as a dimercaptan, any oxidizing agent known to the art to be capable of converting a dimercaptan to a disulfide may be used. Exemplary of such agents are an alkali metal ferricyanide, especially potassium or sodium ferricyanide, oxygen gas, diiodomethane or iodine. The reaction is conducted in a suitable inert solvent, such as aqueous methanol or water, at temperatures from about 0° to about 40° C., under high dilution. The pH is usually maintained at about 7 to about 8. Cyclization may be performed upon the peptide while it is still attached to the support resin or while other functional groups are still protected, but it is preferrably performed on the deprotected free peptide.

Acid addition salts of the peptides are prepared in a standard manner in a suitable solvent from the parent compound and an excess of an acid, such as hydrochloric, hydrobromic, sulfuric, phosphoric, acetic, maleic, succinic or methanesulfonic. The acetate salt form is especially useful. Certain of the compounds form inner salts or zwitterions which may be acceptable. Cationic salts are prepared by treating the parent compound with an excess of an alkaline reagent, such as a hydroxide, carbonate or alkoxide, containing the appropriate cation. Cations such as Na+, K+, Ca++and $NH_4$+are examples of cations present in pharmaceutically acceptable salts.

This invention provides an anti-fibrotic composition which comprises a peptide according to formula (I) or (II) and a pharmaceutically acceptable carrier. Pharmaceutical compositions of the peptides prepared as hereinbefore described and other peptide or polypeptide derivatives of fibronectin, fibrinogen or Von Willebrand's factor, may be formulated as solutions or lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, these peptides may be encapsulated, tableted or prepared in a emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

For buccal administration, the peptides of this invention may also be combined with excipients such as cocoa butter, glycerin, gelatin or polyethylene glycols and molded into a suppository.

This invention also provides a method of inhibiting platelet aggregation and clot formation in a mammal, especially a human, in need thereof, which comprises the internal administration of an effective amount of the antifibrotic peptide and a pharmaceutically acceptable carrier. Indications for such therapy include myocardial infarction, deep vein thrombosis, pulmonary embolism, dissecting anurysm, stroke and other infarct-related disorders. Chronic or acute states of hyper-aggregability, such as disseminated intravascular coagulation (DIC), septicemia, surgical or infectious shock, post-operative and post-partum trauma, cardiopulmonary bypass surgery, incompatible blood transfusion, abruptio placenta, thrombotic thrombocytopenic purpura (TTP), snake venom and immune diseases, are likely to be responsive to such treatment. The anti-fibrotic peptide is administered either orally or parenterally to the patient, in a manner such that the concentration of drug in the plasma is sufficient to inhibit platelet aggregation. The pharmaceutical composition containing the peptide is administered at a dose between about 0.2 to about 50 mg/kg in a manner consistent with the condition of the patient. For acute therapy, parenteral administration is preferred. For persistant states of hyperaggregability, an intravenous infusion of the peptide in 5% dextrose in water or normal saline is most effective, although an intramuscular bolus injection may be sufficient.

For chronic, but noncritical, states of platelet aggregability, oral administration of a capsule or tablet, or a bolus intramuscular injection is suitable. The peptide is administered one to four times daily at a level of about 0.4 to about 50 mg/kg. to achieve a total daily dose of about 0.4 to about 200 mg/kg/day.

This invention further provides a method for inhibiting the reocclusion or an artery or vein following fibrinolytic therapy, which comprises internal administration of an effective amount of an antifibrotic peptide and a fibrinolytic agent to a mammal in need thereof. It has been found that administration of an antifibrotic peptide in fibrinolytic therapy either prevents reocclusion completely or prolongs the time to reocclusion. When used in a method for inhibiting reocclusion of a vessel following fibrinolytic therapy, this invention is intended to encompass not only the peptides set forth above, but other peptides, polypeptides and fragments or derivatives of peptides and polypeptides, which possess the amino acid sequence -RGD- and are capable of binding to the GPIIb-IIIa receptor. Examples of such anti-fibrotic compounds would be derivatives and fragments of fibronectin, fibrinogen and von Willebrands factor. These peptides/polypeptides can be produced as known in the art by recombinant DNA methods or by solid state peptide synthesis or by conventional solution synthesis or solution synthesis. Methods for preparation of fragments of fibronectin have been disclosed (Ruoslahti et al., WO 84/00540; Pierschbacher et al., U.S. Pat. No. 4,589,881; and Rouslahti et al., U.S. Pat. No. 4,661,111) and are incorporated herein by reference. The peptides produced in this manner may be further derivatized by amidation, esterification, alkylation, acetylation or coupling to other natural or unnatural amino acids. Peptides/polypeptides produced in this manner may be formulated as set forth above for parenteral or oral administration.

When used in the context of this invention the term fibrinolytic agent is intended to mean any compound, whether a natural or synthetic product, which directly or indirectly causes the lysis of a fibrin clot. Plasminogen activators are a well known group of fibrinolytic agents. Useful plasminogen activators include, for example, urokinase (UK), pro-urokinase (pUK), streptokinase (SK), tissue plasminogen activator (tPA) and mutants, or variants, thereof, which retain plasminogen activator activity, such as variants in which one or more amino acids have been added, deleted or substituted or in which one or more functional domains have been added, deleted or altered such as by combining the active site of one plasminogen activator, e.g., tPA, with the fibrin binding domain of another plasminogen activator, e.g., one or more Kringle regions from urokinase, or with another fibrin binding molecule such as a Fab fragment of an anti-fibrin IgG. Other illustrative variants include tPA molecules in which one or more glycosylation sites have been altered. Preferred among plasminogen activators are variants of tPA in which the primary amino acid sequence has been altered in the growth factor domain so as to increase the serum half-life of the plasminogen activator. tPA Growth factor variants are disclosed, e.g., by Robinson et al., EP-A-297589 and Browne et al., EP-A-240334 and in a United Kingdom patent application GB88151352, all of which are incorporated by reference herein as though fully set forth. Fibrinolytic agents may be isolated from natural sources, but are commonly produced by traditional methods of genetic engineering.

Useful formulations of tPA, SK, UK and pUK are disclosed, for example, in EP-A 211592, German Patent Application No. 3032606, European Patent Application No. 83103629.8 and U.S. Pat. No. 4,568,543, all of which are incorporated herein by reference. Typically the fibrinolytic agent may be formulated in an aqueous, buffered, isotonic solution, such as sodium or ammonium acetate or adipate buffered at pH 3.5 to 5.5. Additional excipients such as polyvinyl pyrrolidone, gelatin, hydroxy cellulose, acacia, polyethylene, glycol, mannitol and sodium chloride may also be added. Such a composition can be lyophilized.

The pharmaceutical composition may be formulated with both the anti-fibrotic and fibrinolytic in the same container, but formulation in different containers is preferred. When both agents are provided in solution form they can be contained in an infusion/injection system for simultaneous administration or in a tandem arrangement.

Indications for such therapy include myocardial infarction, deep vein thrombosis, pulmonary embolism, stroke and other infarct-related disorders. The anti-fibrotic is administered just prior to, at the same time as, or just after parenteral administraton of tPA or other fibrinolytic agent. It may prove desirable to continue treatment with the anti-fibrotic for a period of time well after reperfusion has been established to maximally inhibit post-therapy reocclusion. The effective dose of tPA, SK, UK or pUK may be from 0.5 to 5 mg/kg and the effective dose of the anti-fibrotic peptide may be from about 0.1 to 25 mg/kg.

For convenient administration of the inhibitor and the fibrinolytic agent at the same or different times, a kit is prepared, comprising, in a single container, such as a box, carton or other container, individual bottles, bags, vials or other containers each having an effective amount of the inhibitor for parenteral administration, as described above, and an effective amount of tPA, or other fibrinolytic agent, for parenteral administration, as described above. Such kit can comprise, for example, both pharmaceutical agents in separate containers or the same container, optionally as lyophilized plugs, and containers of solutions for reconstitution. A variation of this is to include the solution for reconstitution and the lyophilized plug in two chambers of a single container, which can be caused to admix prior to use. With such an arrangement, the fibrinolytic and anti-fibrotic peptide may be packaged separately, as in two containers, or lyophilized together as a powder and provided in a single container.

When both agents are provided in solution form, they can be contained in an infusion/injection system for simultaneous administration or in a tandem arrangement. For example, the platelet aggregation inhibitor may be in an i.v. injectable form, or infusion bag linked in series, via tubing, to the fibrinolytic agent in a second infusion bag. Using such a system, a patient can receive an initial bolus-type injection or infusion, of the anti-fibrotic inhibitor followed by an infusion of the fibrinolytic agent.

The pharmacological activity of the peptides was assessed by the following tests:

Interaction With Fibrinolytic Therapy-Lysis Of A Preformed Human Clot

The human clot lysis assay is used to assess the in vitro effect of anti-fibrotic peptide on tPA induced fibrinolysis. Outdated, citrated, human plasma from the American Red Cross is spun for 20 min. at 1300X g to remove remaining blood cells. A solution consisting of plasma, $^{125}$I-fibrinogen, calcium chloride and thrombin is added to 6 mm tissue culture plates and incubated 15 to 18 hrs. at 37° C. The next morning, each well is rinsed to release the clot. Clots are washed twice with Tris-buffered saline, containing heparin and albumin. Each clot is then added to 1.0 ml of the same plasma used to prepare the clot. tPA is added to tubes over a concentration range of 7 to 250 ng/ml (final concentration). Tubes are incubated at 37° C. with gentle rotation for 4 hrs. At the end of 4 hrs., a 25 µl aliquot is removed and counted to measure $^{125}$I released from the clot. All samples are run in triplicate.

The results of this test are represented graphically in FIG. 1. This demonstrates that the peptide Ac-RGDS-NH$_2$ has no interaction with tPA induced clot lysis.

In Vivo Demonstration Of Inhibition Of Platelet Aggregation

In vivo inhibition of thrombus formation is demonstrated by recording the systemic and hemodynamic effects of infusion of the peptides into anesthetized dogs according to the methods described in Aiken et al., *Prostaglandins*, 19, 629–43 (1980). Briefly, a small Lexan® cylinder is placed around a mechanically damaged left circumflex coronary artery to produce a fixed partial obstruction of 80–90%. Under these conditions, platelets adhere to the exposed subendothelial collagen and aggregate at the obstructed site. Aggregation is assessed as a gradual reduction in blood flow over 2–3 min. until the thrombus is mechanically dislodged from the lumen of the obstructed vessel and coronary blood flow is restored. This process is allowed to repeat itself every 2–3 min. through the control period of the experiment.

The results of such an experiment using Ac-RGDS-NH$_2$ are illustrated in FIG. 2 (*a–c*). Thus the top trace, (*a*), measures arterial blood pressure (mmHg), the middle trace, (*b*), measures phasic coronary blood flow (ml/min.) and the bottom trace, (*c*), measures mean coronary blood flow. During the control period, flow decreases (trace (*b*) and (*c*)) until the clot is shaken loose (SL). The arrow indicates initiation of coronary infusion of Ac-RGDS-NH$_2$ (400 mm at 0.1 ml/mm). This infusion resulted in complete inhibition of thrombus formation until infusion was terminated (second arrow). Termination of infusion results in a decrease in flow as thrombus formation occurs.

Dose dependence of the anti aggregatory activity is demonstrated by observing the effect upon mean coronary blood flow (ml/mm) when the infusion rate of the anti-fibrotic peptide is varied. This is demonstrated in FIG. 3 (*a–c*) for Ac-RGDS-NH$_2$. The top trace, (*a*), shows complete inhibition of thrombus formation (400 mM at 0.052 ml/min.). The middle trace, (*b*), shows moderate inhibition with spontaneous sloughing off of the thrombus X (400 mM at 0.026 ml/min.). The bottom trace, (*c*), shows partial inhibition with prolongation of time to complete blockage (400 mM, 0.013 ml/min.), which required the thrombus to be shaken loose (SL). Again initiation and termination of infusion is depicted by arrows.

Inhibition of Platelet Aggregation

Blood was collected (citrated to prevent coagulation) from, naive, adult mongrel dogs. Platelet rich plasma, PRP, was prepared by centrifugation at 150×g for 10 min. at room temperature. Washed platelets were prepared by centrifuging PRP at 800×g for 10 min. The cell pellet thus obtained was washed twice in Tyrode's buffer (pH 6.5) without Ca$^{2+}$ and resuspended in Tyrode's buffer (pH 7.4) containing 1.8 mM Ca$^{2+}$ at 3×10$^5$ cells/ml. Peptides were added 3 min. prior to the agonist in all assays of platelet aggregation. Final agonist concentrations were 0.1 unit/ml thrombin and 2 µM ADP (Sigma). Aggregation was monitored in a Chrono-Log Lumi-Aggregometer. Light transmittance 5 min. after addition of the agonist was used to calculate percent aggregation according to the formula % aggregation=[(90−CR)÷(90−10)]×100, where CR is the chart reading, 90 is the baseline, and 10 is the PRP blank reading. IC$_{50}$'s were determined by plotting [% inhibition of aggregation] vs. [concentration of peptide]. Peptides were assayed at 200 µM and diluted sequentially by a factor of 2 to establish a suitable dose response curve.

To assess the stability of the peptide to plasma proteases, the peptides were incubated for 3 hrs. (rather than 3 min.) in the PRP prior to addition of the agonist.

The following table is illustrative of the activity of the peptides of this invention upon platelet aggregation.

ANTIAGGREGATORY ACTIVITY

| | | % Activity | Antiaggregatory Activity | |
|---|---|---|---|---|
| Example | Structure | after 3 hr. in PRP | IC$_{50}$, µM PRP/ADP | IC$_{50}$, µM WP/Thrombin |
| 1 | cyclo Ac-Cys-MeArg-Gly-Asp-Ser-Cys-NH$_2$ | 100 | 1.1 | NT |
| 2 | cyclo Ac-Cys-A-g-Gly-Asp-D,L-APmp-NH$_2$ | 100 | 1.53 | NT |
| 3 | cyclo Ac-Cys-Arg-Gly-Asp-Ser-Cys-NH$_2$ | 100 | 32.7 | 54.3 |
| 4 | cyclo Mpr-Arg-Gly-Asp-Ser-Cys-NH$_2$ | NT | 10.9 | NT |
| 5 | cyclo Ac-Cys-MeArg-Gly-Asp-Ser-Pen-NH$_2$ | NT | 1.3 | NT |
| 6 | cyclo Ac-Cys-MeArg-Gly-Asp-(α-Me)Ser-Pen-NH$_2$ | | 76.96 | NT |
| 7 | cyclo Mpr-MeArg-Gly-Asp-Ser-Cys-NH$_2$ | NT | 1.2 | NT |
| 8 | cyclo Ac-Cys-MeArg-Gly-Asp-Cys-NH$_2$ | NT | 0.91 | NT |
| 10 | cyclo Ac-Cys-Arg-Gly-Asp-Pen-NH$_2$ | NT | 4.12 | NT |
| 11 | cyclo Ac-Cys-Arg-Gly-Asp-D-Pen-NH$_2$ | NT | 20.3 | NT |
| 12 | cyclo Ac-Cys-Lys-Gly-Asp-Pen-NH$_2$ | NT | 55.3 | NT |
| 13 | cyclo Ac-Cys-HArg-Gly-Asp-Pen-NH$_2$ | NT | 3.85 | NT |
| 14 | cyclo Ac-Cys-MeArg-Gly-Asp-Pen-NH$_2$ | NT | 0.26 | NT |
| 15 | Ac-Arg-Gly-Asp-Ser-NHEt | NT | >200 | NT |
| 16 | cyclo Ac-Cys-Arg-Gly-Asp-Pen-NHEt | NT | 9.5 | NT |
| 17 | cyclo Ac-Cys-D-Arg-Gly-Asp-Pen-NH$_2$ | NT | 4.10 | NT |

-continued

ANTIAGGREGATORY ACTIVITY

| Example | Structure | % Activity after 3 hr. in PRP | Antiaggregatory Activity $IC_{50}$, μM PRP/ADP | $IC_{50}$, μM WP/Thrombin |
|---|---|---|---|---|
| 18 | cyclo Ac-Cys-MeArg-Gly-Asp-Tyr-Cys-NH$_2$ | NT | 1.49 | NT |
| 24 | cyclo Ac-Cys-(Et$_2$)Arg-Gly-Asp-Pen-NH$_2$ | NT | 81.7 | NT |
| 26 | Ac-MeArg-Gly-Asp-Ser-NH$_2$ | 100 | 7.4 | 28.2 |
| 27 | Ac-Arg-Gly-Asp-Ser-NH$_2$ | 0 | 91.3 | 67.2 |
| 28 | Ac-Arg-Gly-Asp-Tyr-NH$_2$ | 98 | 101.5 | 137 |
| 29 | Ac-Arg-Gly-Asp-NH$_2$ | 54.2 | 137.8 | 356 |
| 30 | Ac-Arg-Gly-Asp-D-Ser-NH$_2$ | 33.3 | 138.8 | >200 |
| 31 | Ac-Arg-Gly-Asp-Val-NH$_2$ | 91.7 | 55.5 | NT |
| 32 | Ac-Arg-Gly-Asp-Nal-NH$_2$ | 100 | 40.5 | NT |
| 33 | Ac-Arg-Arg-Gly-Asp-Phe-NH$_2$ | 5.9 | 112.7 | NT |
| 34 | Ac-Arg-Gly-Asp-NHCH$_2$CH$_2$Ph | 100 | 75.9 | NT |
| 35 | Ac-MeArg-Gly-Asp-Phe-NH$_2$ | 100 | 10.8 | NT |
| 36 | Ac-HArg-Gly-Asp-Ser-NH$_2$ | 33.3 | 68.2 | NT |
| 37 | MeArg-Gly-Asp-Ser-NH$_2$ | NT | 66.3 | NT |
| 38 | HCO-MeArg-Gly-Asp-Ser-NH$_2$ | NT | 6.9 | NT |
| 39 | Gly-MeArg-Gly-Asp-Ser-NH$_2$ | NT | 12.0 | NT |

PRP = platelet rich plasma
WP = washed platelets

The examples which follow are intended to in no way limit the scope of this invention, but are provided to illustrate how to make and use the compounds of this invention.

EXAMPLES

In the examples which follow all temperatures are in degrees centigrade. Amino acid analysis was performed upon a Dionex autoion 100. Analysis for peptide content is based upon amino acid analysis. Mass spectra were performed upon a VG Zab mass spectrometer using fast atom bombardment. EM silica gel thin layer (0.25 mm) plates were used for thin layer chromatography. ODS refers to an octadecylsilyl silica gel chromatographic support. The abbreviations used to represent the eluent composition are B: butanol, A: acetic acid, W: water, E: ethyl acetate, IP: isopropanol, P: pyridine and CA: chloroacetic acid. HPLC was performed upon a Beckman 344 gradient chromatography system with a CRIB recording integrator in either an isocratic or continuous gradient mode. Where indicated, the purity of the peptide is based upon integration of the HPLC chromatogram. MeArg was prepared by the method disclosed by Ali et al., in U.S. Pat. No. 4,687,758 (1987).

Example 1
Preparation of N$^\alpha$-Ac-Cyclo(S,S) Cys-MeArg-Gly-Asp-Ser-Cys-NH$_2$ The protected peptide-resin intermediate, N$^\alpha$-Ac-Cys (SEt)-MeArg(Tos)-Gly-Asp(OChx)-Ser(Bzl)-Cys (4-MBzl)-MBHA, was synthesized by the solid-phase method on 4-methylbenzhydrylamine resin, using an automated Beckman 990 MP synthesizer on 1.0 mmol scale. All of the amino acids were protected as t-buytloxycarbonyl on the amino group, and were coupled sequentially using N,N-dicyclohexylcarbodiimide/1-hydroxybenzotriazole(DCC/HOBt) in the manner set forth by Ali et al. in J. Med. Chem., 29, 984(1986) and J. Med. Chem., 30, 2291(1987). After coupling of the last amino acid, the peptide was acetylated using a mixture of acetic anhydride (10 eq.) and diisopropylethylamine (10 eq.) in dimethyl formamide. The peptide was cleaved from the resin with deprotection of the side chain protecting groups using anhydrous HF (30 mL) in the presence of anisole (3.0 mL) at 0° C. for 60 minutes. After the evaporation of HF in vacuo, the residue was washed with anhydrous ether, and the crude peptide was extracted with 50% acetic acid and was diluted to 2L with deionized water. The pH of the aqueous solution was adjusted to 7.5 with conc. ammonium hydroxide. Under these slightly alkaline conditions, the free thiol generated by removal of the 4 MBzl group from cysteine effectd a nucleophilic displacement of the mercaptoethyl protecting group of the second cysteine to effect intramolecular cyclization of the peptide. An inert gas such as nitrogen or argon is bubbled through the solution to drive off the ethyl mercaptan produced. The cyclization process takes place within 24–48 hours. The reaction solution was then passed through an octadecyl silane (ODS) reversed-phase chromatography column, previously equilibrated with water. The peptide was eluted with 15% acetonitrile/H$_2$O-0.1% TFA solution, to give 678.6 mg (98% crude yield). The peptide was purified by chromatography using a medium pressure ODS reversed-phase column which was eluted with 5% acetontrile/H$_2$O-0.1% TFA solution. The titled peptide eluted in two fractions to give 222.3 mg with >98% purity.

Physical data:
M.F.: $C_{24}$ H$_{40}$ N$_{10}$ O$_{10}$ S$_2$
M.W.: 692.231
FAB: (M+H)$^+$ 693.5, (M–H)$^-$ 692.0
AAA: Asp (1.07); Ser (1.00); Gly (1.00); Cys (2.37)
Peptide content: 67.7%
Chromatography Data:
1. TLC: (B:A:W:E, 1:1:1:1), R$_f$=0.42;
   (B:A:W:P, 15:3:8:10), R$_f$=0.36.
2. HPLC: Altex Ultrasphere® ODS, 4.5mm×25cm, detection at 220 nM.
   Isocratic elution: 2% acetonitrile/H$_2$O-0.1% TFA, k'=0.2.
   Step gradient elution: applied to column equilibrated with H$_2$O-0.1% TFA, 5% acetronitrile/H$_2$O-0.1% TFA 5 min., 50% 20 min.
   k'=1.5.

Substituting Boc-Thr(Bzl) in the above sequence for Boc-Ser(Bzl) produces N$^\alpha$-Ac-Cyclo(S,S) Cys-MeArg-Gly-Asp-Thr-Cys-NH$_2$.

Substituting Boc-D-(Me)Cys into the above sequence for Boc-Ser(Bzl) produces N$^\alpha$-Ac-Cyclo(S,S) Cys-MeArg-Gly-Asp-D-(Me)Cys-Cys-NH$_2$.

Substituting Boc-Val into the above sequence for Boc-Ser(Bzl) produces $N^\alpha$-Ac-Cyclo(S,S) Cys-MeArg-Gly-Asp-Val-Cys-$NH_2$.

Substituting Boc-Nva into the above sequence for Boc-Ser(Bzl) produces N -Ac-Cyclo(S,S) Cys-MeArg-Gly-Asp-Nva-Cys-$NH_2$.

Substituting Boc-Phg in the above sequence for Boc-Ser (Bzl) produces $N^\alpha$-Ac-Cyclo(S,S) Cys-MeArg-Gly-Asp-Phg-Cys-$NH_2$.

Substituting Boc-HPhe into the above sequence for Boc-Ser(Bzl) produces $N^\alpha$-Ac-Cyclo(S,S) Cys-MeArg-Gly-Asp-HPhe-Cys-$NH_2$.

Example 2

Preparation of $N^\alpha$-Ac-Cyclo(S,S) Cys-Arg-Gly-Asp-(D,L)APmp-$NH_2$

The protected peptide-resin intermediate, $N^\alpha$-Ac-Cys(SEt)-Arg(Tos)-Gly-Asp(OChx)-APmp(4-MBzl)-MBHA, was prepared, cleaved, cyclized and isolated in the same manner as Example 1 on 0.5 mmol scale. The peptide was purified by flash chromatography using a medium pressure ODS reversed-phase column eluted with 15% acetonitrile/$H_2O$-0.1% TFA. The titled compound eluted in fractions to give 150.9 mg (45.8%) in >96% purity.

Physical Data:
M.F. $C_{25} H_{41} N_9 O_8 S_2$; M.W.: 659.4
FAB: $(M+H)^{30}$ 660
AAA: Asp (1.00), Gly (1.00), Arg (0.91)
Peptide content: 60.6%
Chromatography Data:
1. TLC: (B:A:W:E, 1:1:1:1), $R_f$=0.67; (B:A:W:P, 15:3:8:10), $R_f$=0.5.
2. HPLC: Altex Ultrasphere® ODS, 4.5mm×25cm, detection at 220 nM.
   Isocratic: 10% acetonitrile/$H_2O$-0.1% TFA, k'=3.24
   Gradient: A: acetonitrile, B: $H_2O$-0.1% TFA, 12–50%A during 20 min., k'=1.97.

Substituting Boc-MeArg(Tos) into the above sequence for Boc-Arg(Tos) produces $N^\alpha$-Ac-Cyclo(S,S) Cys-MeArg-Gly-Asp-(D,L)-APmp-$NH_2$.

Example 3

Preparation of $N^\alpha$-Ac-Cyclo(S,S) Cys-Arg-Gly-Asp-Ser-Cys-$NH_2$

The protected peptide-resin intermediate, $N^\alpha$-Ac-Cys(SEt)-Arg(Tos)-Gly-Asp(OBzl)-Ser(Bzl)Cys(4-MBzl)-MBHA, was synthesized, cleaved and cyclized in the same manner as Example 1 on 1.0 mmol scale. It was lyopholized to give 530 mg (78%). It was purified by flash chromatography using a medium pressure ODS reversed-phase column which was eluted with 1% acetonitrile/$H_2O$-0.1% TFA. This yielded 61 mg of the titled peptide in 90% purity.

Physical Data:
M.F.: $C_{23} H_{38} N_{10} O_{10} S_2$
M.W.: 678.75
FAB: $(M+H)^+$ 679
AAA: Asp (1.00); Ser (0.98); Gly (0.97); Arg (0.90), Cys (1.75)
Peptide content: 86.3%
Chromatography Data:
1. TLC: (B:A:W:E, 1:1:1:1), $R_f$=0.32; (B:W:IP:CA, 6.5:2:1.5:0.3), $R_f$=0.06.
2. HPLC: Vydac 218 TP ODS column, 4.6mm×25cm, detection at 220 nM.
   Gradient: A: acetonitrile, B: $H_2O$-0.1% TFA, 0–50% during 35 min., k'=6.4.

Substituting Boc-Tyr(Brz) for Ser(Bzl) in the above sequence produces $N^\alpha$-Ac-Cyclo(S,S) Cys-Arg-Gly-Asp-Tyr-Cys-$NH_2$.

Substituting Boc-Phe for Boc-Ser(Bzl) in the above sequence produces $N^\alpha$-Ac-Cyclo(S,S) Cys-Arg-Gly-Asp-Phe-Cys-$NH_2$.

Substituting Boc-Met into the above sequence for Boc-Ser(Bzl) produces $N^\alpha$-Ac-Cyclo(S,S) Cys-Arg-Gly-Asp-Met-Cys-$NH_2$.

Substituting Boc-Nle into the above sequence for Boc-Ser(Bzl) produces $N^\alpha$-Ac-Cyclo(S,S) Cys-Arg-Gly-Asp-Nle-Cys-$NH_2$.

Substituting Boc-Nal into the above sequence for Boc-Ser(Bzl) produces $N^\alpha$-Ac-Cyclo(S,S) Cys-Arg-Gly-Asp-Nal-Cys-$NH_2$.

Substituting Boc-Ile into the above sequence for Boc-Ser (Bzl) produces $N^\alpha$-Ac Cyclo(S,S) Cys-Arg-Gly-Asp-Ile-Cys-$NH_2$.

Example 4

Preparation of Cyclo(S,S)Mpr-Arg-Gly-Asp-Ser-Cys-$NH_2$:

The protected peptide-resin intermediate, Mpr(4-MBzl)-Arg(Tos)-Gly-Asp(OChx)-Ser(Bzl)-Cys(SEt)-MBHA, was prepared, cleaved, cyclized and isolated in the same manner as Example 1 on 1.0 mmol scale. The peptide was purified by flash chromatography using a medium pressure ODS reversed-phase column eluted with 3.5% acetonitrile/$H_2O$-0.1% TFA. This yielded 489 mg (79%) of the titled compound in 96% purity.

Physical Data:
M.F.: $C_{21} H_{34} N_9 O_9 S_2$
M.W.: 621.208
FAB: $(M+H)^+$ 622.1; $(M-H)^-$ 620.7
AAA: Asp (1.00), Ser (0.97), Gly (1.00), Cys (0.57), Arg (1.03)
Peptide content: 73.88%
Chromatography Data:
1. TLC: (B:A:W:E, 1:1:1:1), $R_f$=0.42
   (B:A:W:P, 15:3:8:10), $R_f$=0.41
2. HPLC: Altex Ultrasphere® ODS, 4.5mm×25cm, detection at 220 nm.
   Isocratic: 4% acetonitrile/$H_2O$-0.1% TFA, k'=3.6
   Gradient: A: acetonitrile, B: $H_2O$-0.1% TFA, 3–50% A during 20 min., k'=3.3

Example 5

Preparation of $N^\alpha$-Ac-Cyclo(S,S)Cys-MeArg-Gly-Asp-Ser-Pen-$NH_2$:

The protected peptide-resin intermediate, $N^\alpha$-Ac-Cys(SEt)-MeArg(Tos)-Gly-Asp(OChx)-Ser(Bzl)-Pen(4-MBzl)MBHA, was prepared, cleaved, cyclized and isolated in the same manner as Example 1 on 1.0 mmol scale to give 542 mg (75%). It was purified by flash chromatography using a medium pressure ODS reversed-phase column eluted with 6% acetonitrile/$H_2O$-0.1% TFA, to give 47.5 mg of the titled compound in 94% purity.

Physical Data:
M.F.: $C_{26} H_{44} N_{10} O_{10} S_2$
M.W.: 720.27
FAB: $(M+H)^+$ 721.3
AAA: Asp (1.00), Ser (0.96), Gly (1.00), MeArg (0.89)
Peptide content: 78.12%
Chromatography Data:
1. TLC: (B:A:W:E, 1:1:1:1), $R_f$=0.42
   (B:A:W:P, 15:5:10:10), $R_f$=0.41
2. HPLC: Altex Ultrasphere® ODS, 4.5mm×25cm, detection 220 nm.
   Isocratic: 6% acetonitrile/$H_2O$-0.1% TFA, k'=5.66
   Gradient: A: acetonitrile, B: $H_2O$-0.1% TFA, 0–50% A during 20 min., k'=3.19

Example 6
Preparation of $N^\alpha$-Ac-Cyclo(S,S)Cys-MeArg-Gly-Asp-MeSer-Cys-NH$_2$:

The protected peptide-resin intermediate, $N^\alpha$-Ac-Cys(SEt)-MeArg(Tos)-Gly-Asp(OChx)-($\alpha$-Me)Ser(Bzl)-Cys(4-MBz l)-MBHA, was prepared, cleaved, cyclized and isolated in the same manner as Example 1 on 0.5 scale. The peptide was eluted from the reversed phase ODS column using 10% acetonitrile/H$_2$O-0.1% TFA to give 47 mg. It was further purified by preparative HPLC using isocratic conditions, 5.5% acetonitrile/H$_2$O-0.1% TFA on the Altex Ultrasphere® ODS, 5 $\mu$, 10mm×25cm, column with detection at 220 nm, to give 10.6 mg in >96% purity.
Physical Data:
M.F.: $C_{26} H_{42} N_{10} O_{10} S_2$
M.W.: 706.237
FAB: (M+H)$^+$ at 707.5; (M–H)$^-$ at 709.5
AAA: Asp (1.06), Gly (1.00)
Peptide content: 55.85%
Chromatography Data:
1. TLC: (B:A:W:E, 1:1:1:1), R$_f$=0.41
   (B:A:W:P, 15:5:10:10), R$_f$=0.49
2. HPLC: Altex Ultrasphere® ODS, 4.5mm×25cm, detection-at 220 nm.
   Isocratic: 4.5% acetonitrile/H$_2$O-0.1% TFA,
   k'=8.95
   Gradient: A: acetonitrile, B: H$_2$O-0.1% TFA,
   0–50% A during 20 min. k'=5.97

Example 7
Preparation of Cyclo(S,S)Mpr-MeArg-Gly-Asp-Ser-Cys-NH$_2$:

The protected peptide-resin intermediate, Mpr(4-MBzl)MeArg(Tos)-Gly-Asp(OChx)-Ser(0-Bzl)-Cys(SEt)-MBHA, was prepared, cleaved, cyclized and isolated in the same manner as Example 1 on 1.0 mmol scale. The peptide was eluted from the column using 5% acetonitrile/H$_2$O-0.1% TFA, to provide 256.5 mg (40%) of the titled compound. It was purified by Sephadex® G-15 gel filtration using 0.2M acetic acid as eluent. It was further purified by preparative HPLC using gradient condition, A: acetonitrile, B: H$_2$O-0.1% TFA, 5–30% during 10 min., on an Altex Ultrasphere® ODS, 5p, 10 mm×25 cm, column with detection at 220 nm. to give the titled compound in >98% purity.
Physical Data:
M.F.: $C_{22} H_{37} N_9 O_9 S_2$
M.W.: 635.22
FAB: (M+H)$^+$ at 636.2
AAA: Asp (1.00), Ser (0.84), Gly (1.04), Cys (1.48)
Chromatography Data:
1. TLC: (B:A:W:E, 1:1:1:1) R$_f$=0.39
   (B:A:W:P, 15:5:10:10) R$_f$=0.49
2. HPLC: Altex Ultrasphere® ODS, 4.5 mm×25 cm, detection at 220 nm.
   Isocratic: 5% acetonitrile/H$_2$O-0.1% TFA,
   k'=5.93
   Gradient: A: acetonitrile, B: H$_2$O-0.1% TFA,
   0–50% A during 20 min., k'=7.86

Example 8
Preparation of $N^\alpha$-Ac-Cyclo(S,S)Cys-MeArg-Gly-Asp-Cys-NH$_2$:

The protected peptide-resin intermediate, $N^\alpha$-Ac-Cys(4-MBzl)-MeArg(Tos)-Gly-Asp(OChx)-Cys(SEt)-MBHA, was prepared, cleaved, cyclized and isolated in the same manner as Example 1 on 1.0 mmol scale. It was eluted from the ODS reversed phase column using 5% acetonitrile/H$_2$O-0.1% TFA, to provide 780 mg of the titled peptide. It was purified by Sephadex® G-15 gel filtration using 0.2M acetic acid as eluent. It was further purified by preprative HPLC using isocratic conditions, 5% acetonitrile/H$_2$O-0.1% TFA, on an Altex Ultrasphere® ODS column, 5p, 10mm×25cm with detection at 220 nm, to provide the titled compound in >98% purity.
Physical Data:
M.F.: $C_{12} H_{35} N_9 O_8 S_2$
M.W.: 605.21
FAB: (M+H)$^+$ at 606.2; (M–H)$^-$ at 604
AAA: Asp (1.00), Gly (1.13), Cys (2.04)
Peptide content: 77.33%
Chromatography Data:
1. TLC: (B:A:W:E, 1:1:1:1), R$_f$=0.43
   (B:A:W:P, 15:5:10:10), R$_f$=0.56
2. HPLC: Altex Ultrasphere® ODS, 4.5 mm×25cm, detection at 220 nm.
   Isocratic: 5% acetonitrile/H$_2$O-0.1% TFA,
   k'=4.76
   Gradient: A: acetonitrile, B: H$_2$O-0.1% TFA,
   0–50% A during 20 min. k'=7.18

Example 9
Preparation of Cyclo(S,S)Mpr-MeArg-Gly-Asp-Pen-NH$_2$:

The protected peptide-resin intermediate, Mpr(4-MBzl)MeArg(Tos)-Gly-Asp(OChx)-Pen(4-MBzl)-MBHA, was prepared, cleaved and isolated in the same manner as Example 1 on 1.0 nmol scale. The peptide was cyclized using 0.01M K$_3$Fe(CN)$_6$ solution. The peptide was chromatographed on an ODS reversed phase column using 10% acetonitrile/H$_2$O-0.1% TFA, to provide 365 mg (63%) of the titled compound. It was further purified by Sephadex® G-15 gel filtration using 0.2M acetic acid as eluent, to provide the titled compound in >96% purity.
Physical Data:
M.F.: $C_{21} H_{36} N_8 O_7 S_2$
M.W.: 576.22
VAB: (M+H)$^+$ at 577.2; (M–H)$^-$ at 575.3
AAA: Asp (1.00), Gly (1.15), Mpr+Pen (1.55)
Peptde content: 65.77%
Chromatography Data:
1. TLC: (B:A:W:E, 1:1:1:1), R$_f$=0.58
   (B:A:W:P, 15:5:10:10), R$_f$=0.5
2. HPLC: Altex Ultrasphere® ODS, 4.5mm×25cm, detection at 220 nm.
   Isocratic: 10% acetonitrile/H$_2$O-0.1% TFA,
   k'=6.11
   Gradient: A: acetonitrile, B: H$_2$O-0.1% TFA,
   0–5-% A during 20 min. k'=10.93

Example 10
Preparation of $N^\alpha$-Ac-Cyclo(S,S)Cys-Arg-Gly-Asp-Pen-NH$_2$:

The protected peptide-resin intermediate, $N^\alpha$-Ac-Cys(SEt)-Arg(Tos)-Gly-Asp(OBzl)-Pen(4-MBzl)MBHA, was prepared, cleaved, cyclized and isolated in the same manner as Example 1 on 1.0 mmol scale to give 400 mg (65%). It was purified by Sephadex® G-25 partition chromatography, using (B:A:W, 4:1:5) to provide the titled compound in >97% purity.
Physical Data:
M.F.: $C_{22} H_{37} N_9 O_8 S_2$ M.W.: 619.711
FAB: (M+H)$^+$ at 620.2, (M–H)$^-$ at 618.7
AAA: Asp (1.00), Gly (1.01), Cys (1.00), Arg (0.67)
Peptide content: 95.6%
Chromatography Data:
1. TLC: (B:A:W:E, 1:1:1:1), R$_f$=0.37
   (B:W:I:C, 65:20:15:3), R$_f$=0.097
2. HPLC: Vydac 218 TP ODS column, 4.6mm×25cm, detection at 220 nm.
   Isocratic: 6% acetonitrile/H$_2$O-0.1% TFA,
   k'=2.2
   Gradient: A: acetonitrile, B: H$_2$O-0.1% TFA, 0–50% A during 15 min. k'=3.7

Example 11
Preparation of N$^\alpha$-Ac-Cyclo(S,S)Cys-Arg-Gly-Asp-D-Pen-NH$_2$:

The protected peptide-resin intermediate, N$^\alpha$-Ac-Cys(SEt)-Arg(Tos)-Gly-Asp(OBzl)-D-Pen(4-MBzl)-MBHA was prepared, cleaved, cyclized and isolated in the same manner as Example 1 on 1.5 mmol scale. The peptide was purified by flash chromatography using a medium pressure ODS reversed-phase column eluted with 15% methanol/H$_2$O-0.1% TFA. This yielded 50 mg (5.4%) of the titled compound in >96% purity.
Physical Data:
M.F.: C$_{22}$ H$_{37}$ N$_9$ O$_8$ S$_2$
M.W.: 619 711
FAB: (M+H)$^+$ at 620.2 , (M–H)$^-$ at 618.8
AAA: Asp (1.00), Gly (1.03), Arg (0.88)
Peptide content: 54%
Chromatography Data:
1. TLC: (B:A:W:E, 1:1:1:1), R$_f$=0.42
   (B:W:I:C, 65:20:15:3), R$_f$=0.11
2. HPLC: Vydac 218 TP ODS column, 4.6mm×25cm, detection at 220 nm
   Isocratic: 5% acetonitrile/H$_2$O-0.1% TFA,
   k'=2.7
   Gradient: A: acetonitrile/H$_2$O-0.1% TFA, 0–50% A during 15 min., k'=3.3

Example 12
Preparation of N$^\alpha$-Ac-Cyclo(S,S)Cys-Lys-Gly-Asp-Pen-NH$_2$:

The protected peptide-resin intermediate, N$^\alpha$-Ac-Cys(SEt)-Lys(Clz)-Gly-Asp(OBzl)-Pen(4-MBzl)-MBHZ, was prepared, cleaved, cyclized and isolated in same manner as Example 1 on 2.0 mmol scale. The crude peptide was passed through an Amberlite® XAD-2 column, and eluted by 50% acetonitrile/H$_2$O-0.1% TFA. It was purified by flash chromatography using a medium pressure ODS reversed-phase column eluted with 5% acetonitrile/H$_2$O-0.1% TFA. This yielded 180 mg (15%) of the titled compound in >97% purity.
Physical Data:
M.F.: C$_{22}$ H$_{37}$ N$_7$ O$_8$ S$_2$
M.W.: 591.698
FAB: (M+H)$^+$ at 592.3, (M–H)$^-$ at 591
AAA: Asp (1.00), Gly (1.13), Lys (1.09), Cys (2.25)
Chromatography Data:
1. TLC: (B:A:W:E, 1:1:1:1), R$_f$=0.38
2. HPLC: Vydac 218 TP ODS column, 4.6mm×25cm, detection at 220 nm.
   Isocratic: 3% acetonitrile/H$_2$O-0.1% TFA,
   k'=3.5

Gradient: A: acetonitrile, B: H$_2$O-0.1% TFA,
   0–50% A during 15 min. k'-2.9

Example 13
Preparation of N$^\alpha$-Ac-Cyclo(S,S)Cys-HArg-Gly-Asp-Pen-NH$_2$:

To a solution of O-methylisourea hydrogen sulfate (290 mg, 1.7 mmol) in 2.5M solution NaOH, pH adjusted to 11, was added the peptide, N$^\alpha$-Ac-Cys-Lys-Gly-Asp-Pen-NH$_2$ (100 mg, 0.17mmol). After standing overnight at room temperature, the reaction mixture was passed through an Amberlite® XAD-2 column, and eluted with 50% acetonitrile/H$_2$O-0.1% TFA. It was purified by flash chromatography using a medium pressure ODS reversed-phase column eluted with 10% acetonitrile/H$_2$O-0.1% TFA to provide 40 mg (37%) of the titled peptide in 95% purity.
Physical Data:
M.F.: C$_{23}$ H$_{39}$ N$_9$ O$_8$ S$_2$
M.W.: 633.74
FAB: (M+H)$^+$ at 634.2, (M–H)$^-$ at 632.3
AAA: Asp (1.00), Gly (1.16), Cys (2.45)
Peptide content: 68.9%
Chromatography Data:
1. TLC: (B:A:W:E, 1:1:1:1), R$_f$=0.44
   (B:W:I:C, 65:20:15:3), R$_f$=0.19
2. HPLC: Vydac 218 TP ODS column, 4.5mm×25cm, detection at 220 nm.
   Isocratic: 4% acetonitrile/ H$_2$O-0.1% TFA,
   k'=2.0
   Gradient: A: acetonitrile, B: H$_2$O-0.1% TFA,
   0–50% A during 15 min. k'=3.2

Example 14
Preparation of N$^\alpha$-Ac-Cyclo(S,S)Cys-MeArg-Gly-Asp-Pen-NH$_2$:

The protected peptide-resin intermediate, N$^\alpha$-Ac-Cys(SEt)-MeArg(Tos)-Gly-Asp(OBzl)-Pen(4-MBzl)-MBHA, was prepared, cleaved, cyclized and isolated in the same manner as Example 1 on 1.0 mmol scale. It was purified by flash chromatography using a medium pressure ODS reversed-phase column eluted with 5% acetonitrile/H$_2$O-0.1% TFA, to provide 209 mg (35%), of the titled compound in 95% purity.
Physical Data:
M.F.: C$_{23}$ H$_{39}$ N$_9$ O$_8$ S$_2$
M.W.: 633.738
FAB: (M+H)$^+$ at 634.7
AAA: Asp (1.00), Gly (0.98), Cys (1.06)
Peptide content: 66%
Chromatography Data:
1. TLC: (B:A:W:E, 1:1:1:1), R$_f$=0.62
   (B:A:W:P, 15:5:10:10), R$_f$=0.39
2. HPLC: Altex Ultrasphere® ODS, 4.5mm×25cm, detection at 220 nm.
   Isocratic: 5% acetonitrile/H$_2$O-0.1% TFA,
   k'=2.39
   Gradient: A: acetonitrile, B:H$_2$O-0.1% TFA,
   5–50% A during 20 min., k'=4.16

Example 15
Preparation of N$^\alpha$-Ac-Arg-Gly-Asp-Ser-NHEt
a) Preparation of Boc-Ser(Bzl)-NHEt
To a solution of Boc-Ser(Bzl), (6.0 gm, 20.3 mmol) and N-methylmorpholine, 2.3 mL, (20.9 mmol) in 50 mL of THF, was added isobutylchloroformate (2.7 mL, 20.8 mmol), at −15° C. The solution was stirred for a few minutes, and gaseous ethylamine was bubbled through the mixture. The mixture was allowed to stir at −15° C. for 30 min. It was then filtered and the filtrate was concentrated to dryness. The resulting residue was dissolved in ethyl acetate (100 mL), and was washed successively with 1M HCl (2×50 mL), water (50 mL), 10% $Na_2CO_3$ (2×50 mL), and brine (50 mL). The organic layer was dried over anhydrous sodium sulfate, filtered and concentrated to yield 6.0 gm of a white powder. The structure was supported by NMR data.

b) Preparation of Boc-Asp(OBzl)-Ser(Bzl)-NHEt

The Boc protecting group of the compound of Example 15(a) was deprotected by anhydrous TFA (10 mL/gm) at room temperature for 40 min. The TFA was removed, and the residual TFA was determined by weight. Using the procedure of Example 12(a), the titled dipeptide was prepared from Boc-Asp(OBzl) (5.82 g, 18 mmol), Boc-Ser(Bzl) NHEt (10.4 g, 18 mmol), N-methylmorpholine (8 mL, 73 mmol) and isobutylchloroformate (2.4 mL, 18 mmol) to give 8.81 g of glassy material. The structure was supported by NMR.

c) Preparation of Boc-Asp-Ser(Bzl)-NHEt

To a solution of 4.0 g of 15(b) in ethyl acetate (100 mL), and methanol (25 mL) was added 5% $Pd/BaSO_4$ (2.0 g), and the mixture was hydrogenolyzed on the Parr shaker for 30 min. under 45 psi of hydrogen. The mixture was filtered, and the filtrate was concentrated to 3.18 g of a white glassy material. Structure was supported by NMR.

d) Preparation of Boc-Asp(O-benzyl-resin)-Ser(Bzl)-NHEt

The compound of Example 15(c) (1.31 g, 3 mmol) was coupled to a hydroxymethyl resin (1% cross linked, 1 g, 1 mmol), using 4-pyrolidinopyridine (0.15 g, 1 mmol) and DCC (620 mg, 3 mm) in methylene chloride.

e) Preparation of Ac-Arg-Gly-Asp-Ser-NHEt

The peptide-resin intermediate, Ac-Arg-Gly-Asp(OBzl-resin)-Ser(Bzl)-NHEt, was prepared from the compound of Example 15(d) by sequential coupling of Boc-Gly and Boc-Arg(Tos) and was cleaved from the resin and deprotected as described in Example 1. The peptide was purified by flash chromatography using a reversed-phase ODS silica column eluted with 5% acetonitrile/$H_2O$-0.1% TFA to give 173 mg in >95% purity.

Physical Data:
M.F.: $C_{19}H_{34}N_8O_8$
M.W.: 502.53
FAB: $(M+H)^+$ 503.0
AAA: Asp (1.08), Gly (1.00), Ser (1.02), Arg (1.07)
Peptide Content: 76.36%
Chromatography Data:
1. TLC: (B:A:W:E, 1:1:1:1) $R_f$=0.38
   (B:W:IP:CA, 6.5:2:1.5:.3), $R_f$=0.08
2. HPLC: Vydac 218 TP ODS, 4.6mm×25cm, detection at 220 nM.
   Isocratic: 5% acetonitrile/$H_2O$-0.1% TFA, k'=0.4
   Gradient: A: acetonitrile, B: $H_2O$-0.1% TFA, 0–10% A during 10 min, k'=3.5.

Using the same procedure, subsituting di-n-butylamine for ethylamine gives $N^\alpha$-Ac-Arg-Gly-Asp-N(C_4H_9)_2.

Example 16

Preparation of $N^\alpha$-Ac-Cyclo(S,S)Cys-Arg-Gly-Asp-Pen-NHEt:

a) Preparation of Boc-Pen(4-MBzl)-NHEt:

The titled protected amino acid was prepared in the same manner as in Example 15(a) using Boc-Pen(4-MBzl).

b) Preparation of Fmoc-Asp(O-tBut)-Pen(4-MBzl)-NHEt:

The titled compound was prepared according to the procedure of Example 15(b).

c) Preparation of Fmoc-Asp(O-benzyl-resin)-Pen(4-MBzl) NHEt:

The Boc protecting group of the compound of Example 16(b) was deprotected by stirring with anhydrous TFA at room temperature for 40 min. The TFA was removed, and the residual TFA was determined by weight. The resulting residue was recrystallized from EtOAc/Hexane to provide 1.88 g (2.5 mmol) of the TFA salt. It was then coupled to a hydroxymethyl resin (1% cross linked, 1.82 g, 1.0 mmol), using 4-pyrolidinopyridine (catalytic amount) and DCC (2.5 mmol) in methylene chloride.

d) Preparation of $N^\alpha$Ac-Cyclo(S,S)Cys-Arg-Gly-Asp-Pen-NHEt:

The protected peptide-resin intermediate, $N^\alpha$-Ac-Cys(SEt)-Arg(Tos)-Gly-Asp(O-Bzl-resin)-Pen-NHEt, was prepared from the compound of Example 16(c) by sequential coupling of Boc-Gly, Boc-Arg(Tos), Boc-Cys(SEt) and acetylation after deprotection of the Fmoc group by 20% piperidine in DMF. It was then cleaved, cyclized and isolated similar to Example 1. The peptide was purified by flash chromatography using a medium pressure ODS reversed-phase column eluted with 15% acetonitrile/$H_2O$-0.1% TFA, to provide 307 mg (48%) in 97% purity.

Physical Data:
M.F.: $C_{24}H_{41}N_9O_8S_2$
M.W.: 647.77
FAB: $(M+H)^+$ at 648.3, $(M-H)^-$ at 646.7
AAA: Asp (1.00), Gly (1.04), Arg (1.03)
Peptide content: 69.5%
Chromatography Data:
1. TLC: (B:A:W:E, 1:1:1:1), $R_f$=0.53
   (B:W:I:C, 65:20:15:3), $R_f$=0.16
2. HPLC: Vydac 218 TP ODS column, 4.5mm×25cm, detection at 220 nm.
   Isocratic: 9% acetonitrile/$H_2O$-0.1% TFA, k'=1.6
   Gradient: A: acetonitrile, B: $H_2O$-0.1% TFA, 0–50% A during 15 min. k'=3.9

Example 17

Preparation of $N^\alpha$-Ac-Cyclo(S,S)Cys-D-Arg-Gly-Asp-Pen-$NH_2$:

The protected peptide-resin intermediate, $N^\alpha$-Ac-Cys(SEt)-D-Arg(Tos)-Gly-Asp(OBzl)-Pen(4-MBzl)-MBHA, was prepared, cleaved, cyclized and isolated in the same manner as Example 1 on 1.00 mmol scale. It was purified by flash chromatography using a medium pressure ODS reversed-phase column eluted with 6% acetonitrile/$H_2O$-0.1% TFA, to provide 300 mg (50%) of the titled compound in 95% purity.

Physical Data:
M.F.: $C_{22}H_{37}N_9O_8S_2$
M.W.: 619.73
FAB: $(M+H)^+$at 620.4, $(M-H)^-$ at 619
AAA: Asp (1.00), Gly (1.03), Cys (2.42), Arg (1.01)
Peptide content: 71.1%
Chromatography Data:
1. TLC: (B:A:W:E, 1:1:1:1), $R_f$=0.31
   (B:A:W:P, 15:5:10:10), $R_f$=0.54
2. HPLC: Altex Ultrasphere® ODS 4.5mm×25cm, detection at 220 nm.
   Isocratic: 6% acetonitrile/$H_2O$-0.1% TFA, k'=5.2
   Gradient: A: acetonitrile, B: $H_2O$-0.1% TFA, 5–50% A during 20 min. k'=3.9

Example 18

Preparation of $N^\alpha$-Ac-Cyclo(S,S)Cys-MeArg-Gly-Asp-Tyr-Cys-$NH_2$:

The protected peptide-resin intermediate, $N^{\alpha}$-Ac-Cys(SEt)-MeArg(Tos)-Gly-Asp(OBzl)-Tyr(BrZ)-Cys(4-MBzl)MBHA, was prepared, cleaved, cyclized and isolated in the same manner as Example 1 on 1.0 mmol scale. It was purified by flash chromatography using a medium pressure ODS reversed-phase column eluted with 11% acetonitrile/$H_2O$-0.1% TFA, to provide 350 mg (45%) of the titled compound. It was further purified by Sephadex® G-15 gel filtration using 0.2M acetic acid as eluent to provide the titled peptide in 95% purity.

Physical Data:
M.F.: $C_{30} H_{44} N_{10} O_{10} S_2$
M.W.: 768.27
FAB: $(M+H)^+$ at 769.3, $(M-H)^-$ at 767.8
AAA: Asp (1.00), Gly (1.00), Cys (1.91), Tyr (1.02)
Peptide content: 82.75
Chromatography Data:
1. TLC: (B:A:W:E, 1:1:1:1), $R_f$=0.65
   (B:A:W:P, 15:5:10;10), $R_f$=0.78
2. HPLC: Altex Ultrasphere® ODS, 4.5mm×25cm, detection at 220 nm.
   Isocratic: 9% acetonitrile/$H_2O$-0.1% TFA,
   k'=6.4
   Gradient: A: acetonitrile, B: $H_2O$-0.1%
   TFA, 5–50% A during 20 min k'=5.5

Example 19
Preparation of $N^{\alpha}$-Ac-Cyclo(S,S)Pen-MeArg-Gly-Asp-Pen-$NH_2$:

The protected peptide-resin intermediate, $N^{\alpha}$-Ac-Pen(4-MBzl)-MeArg(Tos)-Gly-Asp(OChx)-Pen(4-MBzl)-MBHA, was prepared, cleaved and isolated in the same manner as Example 1 on 1.0 mmol scale. The peptide was cyclized using 0.01% $K_3Fe(CN)_6$ solution. The peptide was eluted from the ODS reversed phase column using 10% acetonitrile/$H_2O$-0.1% TFA, to provide 395 mg (60%) of the titled compound. It was further purified by Sephadex® G-15 gel filtration using 0.2M acetic acid as eluent, to provide the titled peptide in 95% purity.

Physical Data:
M.F.: $C_{25} H_{43} N_9 O_8 S_2$
M.W.: 661.27
FAB: $(M+H)^+$ at 662.3, $(M-H)^-$ at 660.1
AAA: Asp (1.00), Gly (1.03)
Peptide content: 43.7%
Chromatography Data:
1. TLC: (B:A:W:E, 1:1:1:1), $R_f$=0.6
   (B:A:W:P, 15:5:10:10), $R_f$=0.56
2. HPLC: Altex Ultrasphere® ODS, 4.5mm×25cm, detection at 220 nm.
   Isocratic: 10% acetonitrile/$H_2O$-0.1% TFA,
   k'=4.4
   Gradient: A: acetonitrile, B: $H^2O$-0.1% TFA, 1–50% A during 20 min. k'=6.8

Example 20
Preparation of $N^{\alpha}$-Ac-Cyclo(S,S)Pen-Arg-Gly-Asp-Cys-$NH_2$:

The protected peptide-resin intermediate, $N^{\alpha}$-Ac-Pen(4-MBzl)-Arg(Tos)-Gly-Asp(OChx)Cys(SEt)-MBHA, was prepared, cleaved, cyclized and isolated in the same manner as Example 1 on 1.0 mmol scale. The peptide was eluted from the ODS reversed phase column using 5% acetonitrile/$H_2O$-0.1% TFA, to provide 400 mg (65%) of the titled compound. It was further purified by Sephadex® G-15 gel filtration using 0.2M acetic acid solution as eluent, to provide the titled peptide in 95% purity.

Physical Data:
M.F.: $C_{22} H_{37} N_9 O_8 S_2$
M.W.: 619.22
FAB: $(M+H)^+$ at 620.2, $(M-H)^-$ at 618.9
AAA: Asp (1.00), Gly (1.07), Arg (0.85)
Peptide content: 62.4%
Chromatography Data:
1. TLC: (B:A:W:E, 1:1:1:1), $R_f$=0.61
   (B:A:W:P, 15:5:10:10), $R_f$=0.69
2. HPLC: Altex Ulrasphere® ODS 4.5mm×25cm, detecion at 220 nm.
   Isocratic: 3% acetonitrile/$H_2O$-0.1% TFA,
   k'=8.4
   Gradient: A: acetonitrile, B: $H_2O$-0.1% TFA,
   1–50% A during 20 min., k'=5.8

Example 21
Preparation of $N^{\alpha}$-Ac-Cyclo(S,S)Cys-D-Arg-Gly-Asp-Ser-Cys-$NH_2$:

The protected peptide-resin intermediate, $N^{\alpha}$-Ac-Cys(SEt)-D-Arg(Tos)-Gly-Asp(OChx)-Ser(Bzl)-Cys(4-MBzl)MBHA, was prepared, cleaved, cyclized and isolated in the same manner as Example 1 on 1.0 mmol scale. The peptide was eluted from the column using 5% acetonitrile/$H_2O$-0.1% TFA, to provide 370 mg (55%) of the titled compound. It was further purified by Sephadex® G-15 gel filtration using 0.2M acetic acid as eluent, to provide the titled peptide in 95% purity.

Physical Data:
M.F.: $C_{23} H_{38} N_{10} O_{10} S_2$
M.W.: 678.22
FAB: $(M+H)^+$ at 679.2, $(M-H)^-$ at 677.2
AAA: Asp (1.00), Gly (1.13), Ser (0.86), Cys (2.02), Arg (1.21)
Peptide content: 45.5%
Chromatography Data:
1. TLC: (B:A:W:E, 1:1:1:1), $R_f$=0.47
   (B:A:W:P, 15:5:10:10), $R_f$=0.62
2. HPLC: Altex Ultrasphere® ODS, 4.5mm×25cm, detection at 220 nm.
   Isocratic: 3% acetonitrile/$H_2O$-0.1% TFA,
   k'=3.6
   Gradient: A: acetonitrile, B: $H_2O$-0.1% TFA,
   1–50% A during 20 min, k'=5.3

Example 22
Preparation of $N^{\alpha}$-Ac-Cyclo(S,S)Cys-Sar-Arg-Gly-Asp-Pen-$NH_2$:

The protected peptide-resin intermediate, $N^{\alpha}$-Ac-Cys(SEt)-Sar-Arg(Tos)-Gly-Asp(OChx)-Pen(4-MBzl)-MBHA, was prepared, cleaved, cyclized and isolated in the same manner as Example 1 on 1.0 mmol scale. The peptide was eluted from the column using 7% acetonitrile/$H_2O$-0.1% TFA, to provide 600 mg (87%) of the titled compound. It was further purified by Sephadex® G-15 gel filtration using 0.2M acetic acid as eluent to provide the titled peptide in 95% purity.

Physical Data:
M.F.: $C_{25} H_{42} N_{10} O_9 S_2$
M.W: 690.26
FAB: $(M+H)^+$ at 691.2, $(M-H)^-$ at 689
AAA: Asp (1.00), Gly (1.14), Arg (1.04)
Peptide content: 78.8%
Chromatography Data:
1. TLC: (B:A:W:E, 1:1:1:1), $R_f$=0.53
   (B:A:W:P, 15:5:10:10), $R_f$=0.67

2. HPLC: Altex Ultrasphere® ODS, 4.5mm×25cm, detection at 220 nm.

Isocratic: 7% acetonitrile/$H_2O$-0.1% TFA,
$k'=4.2$

Gradient: A: acetonitrile, B: $H_2O$-0.1% TFA,
1–50% A during 20 min., $k'=6.5$

Example 23
Preparation of $N^\alpha$-Ac-Cyclo(S,S)Cys-Arg-Gly-Asp-Cys-$NH_2$:

The protected peptide-resin intermediate, $N^\alpha$-Ac-Cys(SEt)-Arg(Tos)-Gly-Asp(OChx)-Cys(4-MBzl)-MBHA, was prepared, cleaved, cyclized and isolated in the same manner as Example 1 on 1.0 mmol scale. The peptide was eluted from the ODS reversed phase column using 3% acetonitrile/$H_2O$-0.1% TFA, to provide 280 mg (47%) of the titled compound. It was purified by Sephadex® G-15 gel filtration using 0.2M acetic acid as eluent to provide the titled peptide in 95% purity.

Chromatography Data:
1. TLC: (B:A:W:E, 1:1:1:1), $R_f=0.49$
   (B:A:W:P, 15:5:10:10), $R_f=0.45$
2. HPLC: Altex Ultrasphere® ODS, 4.5mm×25cm, detection at 220 nm.

Isocratic: 3% acetonitrile/$H_2O$-0.1% TFA,
$k'=2.7$

Gradient: A: acetonitrile, B: $H_2O$-0.1% TFA,
1–50% A during 20 min., $k'=5.0$

Example 24
Preparation of $N^\alpha$-Ac-Cyclo(S,S)Cys-($Et_2$)Arg-Gly-Asp-Pen-$NH_2$:

The protected peptide-resin intermediate, $N^\alpha$-Ac-Cys(Et)-($Et_2$)Arg-Gly-Asp(OChx)-Pen-MBHA, was prepared, cleaved, cyclized and isolated in the same manner as Example 1 on 1.0 mmol scale. The peptide was eluted from the column using 9% acetonitrile/$H_2O$-0.1% TFA, to provide 590 mg (87%) of the titled peptide. It was further purified by Sephadex® G-15 gel filtration using 0.2M acetic acid as eluent to provide the title peptide in 95% purity.

Physical Data:
M.F.: $C_{26} H_{45} N_9 O_8 S_2$
M.W.: 675.82
FAB: $(M+H)^+$ at 676.4
AAA: Asp (1.00), Gly (1.12)
Peptide content: 51.77%
Chromatography Data:
1. TLC: (B:A:W:E, 1:1:1:1) $R_f=0.45$
   (B:A:W:P, 15:5:10:10) $R_f=0.64$
2. HPLC: Altex Ultrasphere® ODS, 4.6mm×25cm, detection at 220 nm.

Isocratic: 9% acetonitrile/$H_2O$-0.1% TFA,
$k'=3.2$

Gradient: A: acetonitrile, B: $H_2O$-0.1% TFA,
5–50% A during 20 min., $k'=4.2$

Example 25
Preparation of $N^\alpha$-Ac-Cyclo(S,S)Cys-D-MeArg-Gly-Asp-Pen-$NH_2$:

The protected peptide-resin intermediate, $N^\alpha$-Ac-Cys(SEt)-D-MeArg(Tos)-Gly-Asp(OChx)-Pen-MBHA, was prepared, cleaved, cyclized and isolated in the same manner as Example 1 on 1.0 mmol scale. Boc-D-MeArg(Tos), was prepared in the same manner as the L-isomer as described U.S. Pat. No. 4,687,758. The peptide was eluted from the column using 7% acetonitrile/$H_2O$-0.1% TFA, to provide 450 mg (71%) of the titled peptide. It was further purified by Sephadex® G-15 gel filtration using 0.2M acetic acid as eluent, to provide the titled peptide.

Example 26
Preparation of $N^\alpha$-Ac-N a-MeArg-Gly-Asp-Ser-$NH_2$

The protected peptide-resin intermediate, $N^\alpha$-Ac-MeArg(Tos)-Gly-Asp(OBzl)-Ser(Bzl)-BHA was prepared by the solid phase method on a 0.5 mmol scale as described in Example 1. After cleavage with HF and washing with anhydrous ether, the peptide was extracted with glacial acetic acid and lyophilized to yield 75.8 mg (31%). It was purified by Sephadex® G-15 gel filtration using 0.2M acetic acid as eluent. The titled compound eluted in 3 fractions to provide 60.6 mg in >96% purity.

Physical Data:
M.F.: $C_{18} H_{32} N_8 O_8$
M.W.: 488.501
FAB: $(M+H)^+$ 489.5
AAA: Asp(1.00), Ser(0.48), Gly(1.09)
Chromatography Data:
TLC: (B:A:W:E, 1:1:1:1), $R_f=0.25$; (B:A:W:P, 15:5:10:10), $R_f=0.31$.

Example 27
Preparation of $N^\alpha$-Ac-Arg-Gly-Asp-Ser-$NH_2$

The protected peptide-resin intermediate, $N^\alpha$-Ac-Arg(Tos)-Gly-Asp(OBzl)-BHA, was prepared, cleaved and isolated in the same manner as Example 26 on 0.5 mmol scale. The peptide was purified by Counter Current Distribution (CCD) using B:A:W, 4:1:5. 240 transfers yielded 80.8 mg in four fractions.

Physical Data:
M.F.: $C_{17} H_{30} N_8 O_8$
M.W.: 474.474
FAB: $(M+H)^+$ 475
AAA: Asp(0.99), Ser(0.24), Gly(1.03), Arg(1.00)
Chromatography Data:
TLC: (B:A:W:E, 1:1:1:1), $R_f=0.2$; (B:A:W:P, 15:5:10:10), $R_f=0.49$.

Example 28
Preparation of $N^\alpha$-Ac-Arg-Gly-Asp-Tyr-$NH_2$

The protected peptide-resin intermediate, $N^\alpha$-Ac Arg(Tos)-Gly-Asp(OBzl)-Tyr(BrZ)-BHA, was prepared, cleaved and isolated in the same manner as Example 27 on 0.5 mmol scale. The peptide was purified by Sephadex® G-15 gel filtration using 0.2M acetic acid as eluent. This yielded 142.1 mg of the titled peptide.

Physical Data:
M.F.: $C_{23} H_{24} N_8 O_8$
M.W.: 550.57
FAB: $(M+H)^+$ 551
AAA: Asp(1.00), Gly(1.02), Tyr(1.00), Arg(0.90)
Chromatography Data:
TLC: (B:A:W:E, 1:1:1:1), $R_f=0.41$; (B:A:W:P, 15:5:10:10), $R_f=0.4$.

Example 29
Preparation of $N^\alpha$-Ac-Arg-Gly-Asp-$NH_2$

The protected peptide-resin intermediate, $N^\alpha$-Ac-Arg($NO_2$)-Gly-Asp(OBzl)-BHA, was prepared, cleaved and isolated in the same manner as Example 27 on 0.5 mmol scale. It was purified by CCD using B:A:W, 4:1:5, to give 98.6 mg in four fractions. The peptide was further purified by Sephadex® G-15 gel filtration using 0.2M acetic acid as eluent to give 65.7 mg in several fractions.

Physical Data:
M.F.: $C_{14} H_{25} N_7 O_6$
M.W.: 387.389
FAB: $(M+H)^+$ 388
AAA: Asp(1.00), Gly(1.13), Arg(0.93)
Chromatography Data:
TLC: (B:A:W:E, 1:1:1:1), $R_f$=0.2; (B:A:W:P, 15:5:10:10), $R_f$=0.44.

Example 30

Preparation of $N^\alpha$-Ac-Arg-Gly-Asp-D-Ser-$NH_2$

The protected peptide-resin intermediate, $N^\alpha$-Ac-Arg(Tos)-Gly-Asp(OBzl)-D-Ser(Bzl)-BHA, was prepared, cleaved and isolated in the same manner as Example 27 on a 1.0 mmol scale. It was purified by flash chromatography using a medium pressure ODS reversed-phase column which was eluted with 0.5% acetonitrile/$H_2O$-0.1% TFA. This provided 337 mg of the titled peptide in 95% purity.
Physical Data:
M.F.: $C_{17} H_{30} N_8 O_8$
M.W.: 474.474
FAB: $(M+H)^+$ 475.3; $(M-H)^-$ 473.5
AAA: Asp(1.00), Ser(0.99), Gly(0.96), Arg(1.01)
Peptide content: 44.8%
Chromatography Data:
1. TLC: (B:A:W:E, 1:1:1:1), $R_f$=0.3.
2. HPLC: Vydac 218 TP ODS column, 4.6mm×25cm, detection at 220 nM.
   Gradient: A: acetonitrile, B: $H_2O$-0.1% TFA, 0–50% A during 30 min., k'=3.4.

Example 31

Preparation of $N^\alpha$-Ac-Arg-Gly-Asp-Val-$NH_2$

The protected peptide-resin intermediate, $N^\alpha$-Ac-Arg(Tos)-Gly-Asp(OBzl)-Val-MBHA, was prepared, cleaved and isolated in a manner similar to Example 27 on 1.0 mmol scale. It was purified by flash chromatography using a medium pressure ODS reversed-phase column which was eluted with 15% methanol/$H_2O$-0.1% TFA. This provided 125 mg of the titled peptide in >95% purity.
Physical Data:
M.F.: $C_{19} H_{34} N_8 O_7$
M.W.: 486.528
FAB: $(M+H)^+$ 487.3; $(M-H)^-$ 485.9
AAA: Asp(1.00), Gly(0.99), Val(1.06), Arg(0.96)
Peptide content: 79.6%
Chromatography Data:
1. TLC: (B:A:W:E, 1:1:1:1), $R_f$=0.43; (B:W:IP:CA, 6.5:2:1.5:0.3), $R_f$=0.11.
2. HPLC: Vydac 218 TP ODS column, 4.6mm×25cm, detection at 220 nM.
   Isocratic: 5% acetonitrile/$H_2O$-0.1% TFA, k-=1.3.
   Gradient: A: acetonitrile, B: $H_2O$-0.1% TFA, 6–50% during 15 min., k'=0.84.

Example 32

Preparation of $N^\alpha$-Ac-Arg-Gly-Asp-Nal-$NH_2$

The protected peptide-resin intermediate, $N^\alpha$-Ac-Arg(Tos)-Gly-Asp(OBzl)-Nal-MBHA, was prepared, cleaved and isolated in the same manner as in Example 27, on a 1.0 mmol scale. It was purified by chromatography using a medium pressure ODS reversed-phase column which was eluted with 40% methanol/$H_2O$-0.1% TFA. This provided 57 mg of the titled peptide in >98% purity.
Physical Data:
M.F.: $C_{27} H_{36} N_8 O_7$
M.W.: 584.632
FAB: $(M+H)^+$ 585.3; $(M-H)^-$ 583.9
AAA: Asp(1.00), Gly(0.99), Arg and Nal present but co-elute
Peptide content: 81.3%
Chromatography Data:
1. TLC: (B:A:W:E, 1:1:1:1), $R_f$=0.60; (B:W:IP:CA, 6.5:2:1.5:0.3), $R_f$=0.23.
2. HPLC: Vydac 218 TP ODS column, 4.6mm×25cm, detection at 220 nM.
   1 Isocratic: 18% acetonitrile/$H_2O$-0.1% TFA, k'=1.2.
   Gradient: A: acetonitrile, B: $H_2O$-0.1% TFA, 15–50% A during 15 min., k'=2.1.

Substituting Boc-(Me)Thr for Boc-Nal in this procedure gives $N^\alpha$-Ac-Arg-Gly-Asp-(Me)Thr-$NH_2$.

Substituting Boc-Nva for Boc-Nal in this procedure gives $N^\alpha$-Ac-Arg-Gly-Asp-Nva-$NH_2$.

Substituting Boc-Nle for Boc-Nal in this procedure gives $N^\alpha$-Ac-Arg-Gly-Asp-Nle-$NH_2$.

Example 33

Preparation of $N^\alpha$-Ac-Arg-Arg-Gly-Asp-Phe-$NH_2$

The protected peptide-resin intermediate, $N^\alpha$-Ac-Arg(Tos)-Arg(Tos)-Gly-Asp(OChx)-Phe-BHA, was prepared, cleaved and isolated in the same manner as Example 27 on a 1.0 mmol scale. It was purified by flash chromatography using a medium pressure ODS reversed phase column which was eluted with 8% acetonitrile/$H_2O$-0.1% TFA. This provided 303.4 mg of the titled peptide in 98% purity.
Physical Data:
M.F.: $C_{29} H_{46} N_{12} O_8$
M.W.: 690.356
FAB: $(M+H)^+$ 691; $(M-H)^-$ 690
AAA: Asp(1.00), Gly(1.00), Phe(0.91), Arg(1.89)
Peptide content: 56.3%
Chromatography Data:
1. TLC: (B:A:W:E, 1:1:1:1), $R_f$=0.4; (B:A:W:P, 15:3:8:10), $R_f$=0.4.
2. HPLC: Ultrasphere® ODS, 4.6mm×25cm, detection at 220 nM.
   Isocratic: 10% acetonitrile/$H_2O$-0.1% TFA, k'=2.78.
   Gradient: A: acetonitrile, B: $H_2O$-0.1% TFA, 10–50% A during 20 min., k'=2.8.

Substituting Boc-HArg(Tos) for Boc-Arg(Tos) in the fifth residue added and Boc-(4'-Me)Phe for Boc-Phe in the first residue in the above synthetic sequences gives $N^\alpha$-Ac-HArg-Arg-Gly-Asp-(4'-Me)Phe-$NH_2$.

Substituting Boc-($Et_2$)Arg in the fifth residue added to the resin and Boc-His(Tos) for Boc-Phe in the first residue in the above synthetic sequence gives $N^\alpha$Ac-($Et_2$)Arg-Arg-Gly-Asp-His-$NH_2$.

Substituting Boc-Ala for Boc-Arg(Tos) in the fifth residue added and Boc-Ile for Boc-Phe in the first residue in the above synthetic sequence gives $N^\alpha$-Ac-Ala-Arg-Gly-Asp-Ile-$NH_2$.

Example 34

Preparation of $N^\alpha$-Ac-Arg-Gly-Asp-NH-CH -$CH_2$-$C_6H_5$
a) Preparation of Boc-Asp(OBzl)-NH-$(CH_2)_2C_6H_5$ To a stirred solution of Boc-Asp(OBzl), 5.0 g (15.5 mmol) and N-methyl morpholine (15.5 mmol) in 50 mL of dry THF under an Ar atmosphere was added isobutylchloroformate (15.5 mmol) at −15° C. After a few minutes, phenethylamine 2.0 mL (15.5 mmol) in 15 mL of dry THF was added. The mixture was maintained at −15° C. for 15 min. and allowed to warm to room temperature. After stirring for an additional 2 hours, the reaction mixture was filtered and the filtrate was concentrated in vacuo to dryness. The resulting residue was dissolved in ethyl acetate (100 mL) and washed successively with 1M HCl (2×50 mL), water (50 mL), 10% sodium carbonate (2×50 mL), and brine (50 mL). The organic layer was dried over sodium sulfate, filtered and concentrated to yield 5.59 gm (85%) of an amorphous white solid.

b) Preparation of Boc-Gly-Asp(OBzl)-NH(CH$_2$)$_2$C$_6$H$_5$

The Boc-protecting group of the compound of Example 12(a) (4.18 g, 12.8 mm) was removed by treatment with anhydrous TFA (10 mL/g) at room temperature for 30 minutes. TFA was removed in vacuo and the residual TFA was determined by weight. Boc-Gly (2.24 gm, 12.8 mmol) was coupled to the free amine using the method of 12(a). It was purified by chromatography using a silica column, which was eluted with a 3:1 ethyl acetate-hexane mixture to yield 3.35 g (54%) of a light yellow glassy material.

c) Preparation of Boc-Arg(Tos)-Gly-Asp(OBzl)-NH(CH$_2$)$_2$C$_6$H$_5$

The Boc- protecting group of the compound of Example 12(b) (2.61 g, 6.8 mm) was removed and the resulting dipeptide was coupled to Boc-Arg(Tos) (3.4 g, 6.8 mm) by the method of Example 12(b). It was purified by flash chromatography using a silica column which was eluted with a 1:1 mixture of ethyl acetate-isopropanol, to yield 3.41 g (63%) of white glassy material.

d) Preparation of Ac-Arg(Tos)-Gly-Asp(OBzl)NH(CH$_2$)$_2$C$_6$H$_5$

The compound of Example 12(c) was deprotected as described in Example 12(b). The free base (2.92 g, 4.2 mmol) and acetic anhydride (2.0 mL, 21.2 mmol), were dissolved in 30 mL DMF and treated with diisopropylethylamine 0.73 mL (4.2 mmol). The reaction mixture was stirred for 30 minutes and was concentrated in vacuo to dryness. This residue was purified by flash chromatography using a silica column, which was eluted with a 1:1 ethyl acetate-isopropanol mixture to yield 2.94 g (95%) of a white glassy material.

e) Preparation of Ac-Arg-Gly-Asp-NH-(CH$_2$)$_2$C$_6$H$_5$

The protected peptide of Example 12(d) (2.5 g) and anisole (2.5 mL) were treated with anhydrous HF (25 mL) at 0° C. for 30 minutes. After evaporation of the HF, the peptide-anisole mixture was treated with 1M acetic acid (3×50 mL) and the aqueous was washed with anhydrous ether (3×100 mL). The aqueous extract was lyophilized to give 1.52 g. It was purified by flash chromatography using a ODS column eluted with 40% methanol/H$_2$O-0.1% TFA. This yielded 326 mg of the titled peptide in 97% purity.
Physical Data:
M.F.: C$_{22}$H$_{33}$N$_7$O$_6$
M.W.: 491.547
FAB: (M+H)$^+$ 492.1; (M−H)$^-$ 490.6
AAA: Asp(0.51), Gly(0.99), Arg(1.00)
Peptide content: 81.2%
Chromatography Data:
1. TLC: (B:A:W:E, 1:1:1:1), R$_f$ 0.58; (B:W:IP:CA, 6.5:2:1.5:0.3), R$_f$ 0.17.
2. HPLC: Vydac 218 TP ODS column, 4.6mm×25cm, detection at 220 nM.
   Isocratic: 12% acetonitrile/H$_2$O-0.1% TFA, k'=2.3.
   Gradient: A: acetonitrile, B: H$_2$O-0.1% TFA,
   10–50% A during 15 min., k'=2.2.

Using the same procedure, substituting aniline for phenethylamine gives N$^\alpha$-Ac-Arg-Gly-Asp-NHC$_6$H$_5$ Example 35
Preparation of N$^\alpha$-Ac-MeArg-Gly-Asp-Phe-NH$_2$ The protected peptide-resin intermediate, N$^\alpha$-Ac-MeArg(Tos)-Gly-Asp-Phe-BHA was prepared, cleaved from the resin, isolated and purified in the same manner as in Example 26 to yield the titled peptide.
Physical Data:
M.F.: C$_{24}$H$_{36}$N$_8$O$_7$
M.W.: 548.270
FAB: (M+H)$^+$ 549.2, (M−H)$^-$ 547.8
AAA: Asp (1.00), Gly (1.00), Phe (1.05), MeArg (1.18)
Chromatography Data:
1. TLC: (B:A:W:E, 1:1:1:1), R$_f$=0.52
   (B:A:W:P, 15:3:8:10), R$_f$=0.46
2. HPLC: Ultrasphere® ODS, 4.6mm×25cm, detection at 220 nM
   Isocratic: 10% acetonitrile/H$_2$O-0.1% TFA,
   k'=3.43
   Gradient: A: acetonitrile, B: H$_2$O-0.1% TFA,
   10–50% A during 20 min., k'=3.6.

Preparation of N$^\alpha$Ac-HArg-Gly-Asp-Ser-NH$_2$

The protected peptide-resin intermediate, N$^\alpha$-Ac-Lys(Clz)-Gly-Asp(OBzl)-Ser(Bzil)-BHA, was prepared, cleaved from the resin and isolated in the same manner as in Example 26 to yield N$^\alpha$-Ac-Lys-Gly-Asp-Ser-NH$_2$. To a solution of the peptide(100 mg, 0.197mm) dissolved in 2 ml of carbonate buffer (pH=10.5), a solution of O-methyl isourea hydrogen sulfate(0.34 g, 1.97 mmol) dissolved in 0.1M NaOH (1 ml, adjusted to pH 11 with 4M NaOH) was added. After standing overnight at room temperature, the reaction was twice chromatographed (Sephadexe® G-10, swollen in H$_2$O, eluted with 0.1M aqueous acetic acid) and the purified peptide was lyophilized to yield 48 mg of the titled peptide.
Physical Data:
M.F.: C$_{18}$H$_{32}$N$_8$O$_8$
M.W.: 488.50
FAB: (M+H)$^+$ 489.2, (M−H)$^-$ 487.7
AAA: Asp (1.00), Ser(0.97), Gly (0.99), Cys (0.21), HArg (0.88)
Chromatography Data:
1. TLC: (B:A:W:E, 1:1:1:1), R$_f$=0.33;
   (B:W:IP:CA, 6.5:2:1.5:0.3), R$_f$=0.04
2. HPLC: Altex Ultrasphere® ODS, 4.5mm×25cm, detection at 220 nM.
   Isocratic: 3% acetonitrile/H$_2$O-0.1% TFA,
   k'=0.8.
   Gradient: A: acetonitrile, B: H$_2$O-0.1% TFA,
   0–50% A during 15 min., k'=2.1

Example 37
Preparation of N$^\alpha$-MeArg-Gly-Asp-Ser-NH$_2$

The protected peptide-resin intermediate, MeArg(Tos)-Gly-Asp(OBzl)-Ser(Bzl)-BHA was prepared and cleaved from the resin in the same manner as in Example 26, with the omission of the acetylation step. The free peptide was purified in the same manner as Example 26 to yield the titled peptide.
Physical Data:
M.F.: C$_{16}$H$_{30}$N$_8$O$_7$
M.W.: 446.22
FAB: (M+H)$^+$ 447.2, (M−H)$^-$ 445.6
AAA: Asp (1.00), Ser (0.95), Gly (1.00), MeArg (1.00)
Peptide Content: 76.74%
Chromatography Data:
1. TLC: (B:A:W:E, 1:1:1:1), R$_f$=0.26
   (B:A:W:P, 15:5:10:10), R$_f$=0.31
2. HPLC: Ultrasphere® ODS, 4.6mm×25cm, detection at 220nM Isocratic: H$_2$O-0.1% TFA, k'=0.66
Gradient: A: acetonitrile, B: H$_2$O-0.1% TFA,
0–50% A during 20 min., k'=0.64

Example 38
Preparation of N$^\alpha$-Formyl-MeArg-Gly-Asp-Ser-NH$_2$

The protected peptide intermediate MeArg(Tos)-Gly-Asp(OBzl)-Ser(Bzl)-BHA was prepared in the usual manner on a 0.5 mmol scale. After deprotection of the terminal amino group with HF, the resin-supported peptide was treated with a mixture of acetic anhydride (1 ml) in formic acid (98%, 7 ml). Subsequent cleavage from the resin yielded the titled peptide.
Physical Data:
M.F.: C$_{17}$H$_{30}$N$_8$O$_8$
M.W.: 474.219
AAA: Asp (1.00), Ser (0.97), Gly (0.98)
Peptide Content: 78.15%
Chromatography Data:
1. TLC: (B:A:W:E, 1:1:1:1) R$_f$=0.37
   (B:A:W:P, 15:5:10:10) R$_f$=0.34
2. HPLC: Ultrasphere® ODS, 4.6mm×25cm, detection at 220 uM Isocratic: 1% acetonitrile/H$_2$O-0.1% TFA,
k'=2.02, 2.69 (cis/trans N-formyl isomers)
Gradient: A: acetonitrile, B: H$_2$O-0.1% TFA,
0–50% A during 20 min., k'=2.17

Example 39
Preparation of Gly-MeArg-Gly-Asp-Ser-NH$_2$

The protected peptide-resin intermediate, Boc-Gly-MeArg(Tos)-Asp(OChx)-Ser(Bzl)-BHA, was prepared and cleaved from the resin as in Example 26. The free peptide was purified by flash chromatography using a medium pressure ODS reversed-phase column eluted with 1% acetonitrile/H$_2$O-0.1% TFA. This yielded 406 mg (80%),in four fractions, in >95% purity.
Physical Data:
M.F. : C$_{18}$ H$_{33}$ N$_9$ O$_8$
M.W. : 503.245
FAB : (M+H)$^+$ 504, (M–H)$^-$ 502
AAA : Asp (1.00), Ser(0.94), Gly(1.96), N-MeArg(0.98)
Peptide content: 69.97%
Chromatography Data:
1. TLC : (B:A:W:E, 1:1:1:1), R$_f$=0.29
2. HPLC : Altex Ultrasphere® ODS, 4.5mm×25cm, detection at 220 nm.

Isocratic : 1% acetonitrile/H$_2$O-0.1% TFA,
k'=1.07
Gradient :A: acetonitrile, B: H$_2$O-0.1%TFA,
0–50% A during 20 min.,k'=2.35

Example 40
Preparation of Ala-MeArg-Gly-Asp-Ser-NH$_2$

The protected peptide resin intermediate, Ala-MeArg(Tos)-Gly-Asp(OBzl)-Ser(Bzl)-BHA is prepared in the same manner as in Example 26, with the omission of the acetylation step. The linear peptide is cleaved from the resin with HF in the usual manner to yield the titled peptide.

Example 41
Preparation of N$^\alpha$-Ac-Ala-Arg-Gly-Asp-OCH$_3$

Boc-Asp-OMe is coupled to a chloromethyl resin using the cesium salt method., to yield Boc-Asp(O-benzyl resin)-OMe, in which aspartic acid is bound to the resin through its side chain carboxyl group. 3 equivalents of each of the protected amino acids (Boc-Gly, Boc-Arg(Tos) and Boc-Ala) are dissolved in dimethyl formamide and coupled sequentially using equimolar amounts of dicyclohexylcarbodiimide and 1-hydroxybenzotriazole. The extent of coupling is determined by qualitative ninhydrin analysis of an aliquot, and couplings are repeated when necessary. The Boc groups are removed by treatment with a 1:1 mixture of trifluoroacetic acid/methylene chloride and, after washing with methylene chloride, the free amine is generated using 5% diisopropyl ethyl amine/methylene chloride. After the final coupling and removal of the Boc group, the peptide/resin is washed with dimethyl formamide and methylene chloride and dried. The peptide is acetylated using a mixture of acetic anhydride (10 eq) and diisopropyl ethylamine (10 eq). The peptide is deprotected and cleaved from the resin by treatment with HF in the presence of anisole at 0° for 1 hr. The HF is removed by evaporation at 0° , the residue is washed with diethyl ether (4x, discarded) and purified by reversed phase hplc, to afford the titled compound.

Example 42
Preparation of N$^\alpha$-Ac-Cyclo(S,S) Cys-Abu-Arg-Gly-Asp-Pen-NH$_2$ The protected peptide-resin intermediate, N$^\alpha$-Ac-Cys(SEt)-Abu-Arg(Tos)-Gly-Asp(OBzl)-Pen(4-MBzl)MBHA, is prepared, cleaved, cyclized, and isolated in the same manner as Example 3. The peptide is purified by flash chromatography using a medium pressure ODS reversed-phase column to yield the titled compound.

Substituting Boc-(Et$_2$)Arg for Boc-Abu as the fifth residue in the above synthetic sequence gives N$^\alpha$-Ac-Cyclo(S, S) Cys-(Et$_2$)Arg-Arg-Gly-Asp-Pen-NH Substituting Boc-(α-Me)Ala for Boc-Abu as the fifth residue in the above synthetic sequence gives N$^\alpha$-Ac-Cyclo (S,S) Cys-(α-Me)Ala-Arg-Gly-Asp-Pen-NH$_2$.

Example 43
Preparation of N$^\alpha$-Ac-Cyclo(S,S) Cys-MeArg-Gly-Asp-Cys-OCH$_3$ a) Preparation of H$_2$N-Asp(O-benzyl-resin)Cys(4-MeBzl)-OCH$_3$ H$_2$N-Cys(4-MBzl)-OMe is coupled with 3 equivalents of Fmoc-Asp(4-tBuO) in DMF using 3 equivalents of 1-HOBT and 3 equivalents of dicyclohexylcarbodiiamide. After 3 hrs. the DMF is evaporated in vacuo and the residue is triturated with ethyl acetate and filtered. The filtrate is washed with 5% aqueous sodium bicarbonate and water. The organic layer is dried over magnesium sulfate, filtered and the solvent is removed in vacuo. The protected dipeptide is further purified by silica gel chromatography.

Fmoc-Asp(4-tBuO)-Cys(4-MBzl)-OMe is treated with 50% TFA/methylene chloride at 0° for 1 hr. and the solvent is evaporated in vacuo. The residue is redissolved in methylene chloride, washed three times with water and the organic layer is dried briefly over MgSO4. Filtration and evaporation of the solvent yields Fmoc-Asp-Cys(4-MBzl) OMe.

The free carboxylic acid of the dipeptide is coupled to a chloromethyl resin using the cesium salt method as set forth by Gisin et al., Helv. Chim. Acta, 56, 1476 (1973). The resin supported dipeptide is treated with 20% piperidine in DMF (3×10 min.). The resin is washed three times with DMF to yield the titled resin supported dipeptide.

b) Preparation of N$^\alpha$-Acetyl-Cyclo(S,S) Cys-MeArg-Gly-Asp-Cys-OCH$_3$

The resin supported dipeptide produced in Example 43(a) is coupled sequentially to Boc-Gly, Boc-MeArg(Tos) and Boc-Cys(SEt), acetylated, cleaved from the resin and cyclized using the procedure of Example 1. The titled peptide is purified using reversed phase hplc.

Employing an identical procedure, except starting with H$_2$N-Cys(4-MBzl)-OEt and substituting (α-Me)HArg(Tos) in the above synthetic sequence, gives N$^\alpha$-Acetyl-Cyclo(S,S) Cys-(α-Me)HArg-Gly-Asp-Cys-OEt.

Example 44

Preparation of N$^\alpha$-Acetyl-Cyclo(S,S) Cys-MeArg-Gly-Asp-Cys-NHEt a) Preparation of H$_2$N-Cys(4-MBzl)-NHEt Boc-Cys(4-MBzl)-OCH$_3$ is dissolved in methanol, cooled to 0° and 1 volume of ethyl amine (precooled to 0°) is added. The reaction mixture is tightly stoppered and stirred at room temperature for eight days. The reaction is recooled to 10° C., vented and the solvent is removed in vacuo. The residue is dissolved in methylene chloride, treated with one volume of TFA and stirred for 1 hr. at room temperature. The titled ethyl amide is purified by silica gel chromatography. Preparation of H$_2$N-Asp(O-benzyl-resin)-Cys(4-MBzl)-NHEt b) The ethyl amide of example 44(a) is substituted for H$_2$N-(4-MBzl)Cys-OMe in the procedure of 21(a), coupled to Fmoc-Asp(4-tBuO), linked to a chloromethyl resin and the free amine liberated to produce the titled compound. Preparation of N$^\alpha$-Ac-Cyclo(S,S) Cys-MeArg-Gly-Asp-Cys-NHEt c) The resin supported dipeptide of Example 44(b) is coupled sequentially to Boc-Gly, Boc-MeArg(Tos) and Boc-Cys(SEt), acetylated, cleaved from the resin and cyclized using the procedure of Example 1. The titled pentapeptide is purified using reversed phase hplc.

Employing the same procedure, except substituting isopropyl amine for ethylamine and beginning the procedure with Boc-Pen(4-MBzl)-OCH yields N$^\alpha$-Ac-Cyclo(S,S) Cys-MeArg-Gly-Asp-Pen-NHC$_3$H$_7$.

Example 45

Substituting the appropriate protected amino acids in the above synthetic sequences of Examples 4 or 11 yields the following linear peptides as follows:
a) N$^\alpha$-Ac-Pro-Arg-Gly-Asp-NH$_2$;
b) N$^\alpha$-Ac-MeArg-Gly-Asp-Nle-NH$_2$;
c) N$^\alpha$-Ac-MeArg-Gly-Asp-Met-NH$_2$;
d) N$^\alpha$-Ac-HArg-Gly-Asp-Leu-NH$_2$;
e) N$^\alpha$-Ac-MeArg-Gly-Asp-Trp-NH$_2$;
f) N$^\alpha$-Ac-MeArg-Arg-Gly-Asp-Thr-NH$_2$;
g) N$^\alpha$-Ac-Ala-MeArg-Gly-Asp-(Me)Ser-NH$_2$;
h) N$^\alpha$-Ac-Arg-(Et$_2$)Arg-Gly-Asp-Ala-NH$_2$;
i) N$^\alpha$-Ac-Abu-MeArg-Gly-Asp-D-Phe-NH$_2$;
j) N$^\alpha$-Ac-MeArg-Gly-Asp-D-(Et)Tyr-NH$_2$;
k) N$^\alpha$-Ac-Arg-Gly-Asp-HPhe-NH$_2$; and
l) N$^\alpha$-Ac-MeArg-Gly-Asp-(Me)Cys-NH$_2$.

Example 46

Substituting the appropriate protected amino acids in the above synthetic sequences according to Example 1 or Example 20 yields the following cyclic peptides as follows:
a) N$^\alpha$-Ac-Cyclo(S,S)-Cys-MeArg-Gly-Asp-Cys-NH$_2$;
b) N$^\alpha$-Ac-Cyclo(S,S)-Cys-HArg-Gly-Asp-Cys-NH$_2$;
c) N$^\alpha$-Ac-Cyclo(S,S)-D,L-APmp-Arg-MeArg-Gly-Asp-Pen-NH$_2$;
d) N$^\alpha$-Ac-Cyclo(S,S)-Cys-MeArg-Arg-Gly-Asp-Cys-NH$_2$;
e) N$^\alpha$-Ac-Cyclo(S,S)-Pen-Pro-Arg-Gly-Asp-Cys-NH$_2$;
f) Cyclo(S,S)-Mpa-Arg-(Et$_2$)Arg-Gly-Asp-(4'-Cl)Phe-D,L-APmp-NH$_2$
g) N$_\alpha$-Ac-Cyclo(S,S)-Pen-Ala-MeArg-Gly-Asp-Trp-Cys-NH$_2$
h) N$^\alpha$-Ac-Cyclo(S,S)-Cys-HArg-Arg-Gly-Asp-Ala-Cys-NH$_2$;
i) N$^\alpha$-Ac-Cyclo(S,S)-Cys-MeArg-Gly-Asp-(Me)Thr-Cys-NH$_2$;
j) N$^\alpha$-Ac-Cyclo(S,S)-Cys-HArg-Gly-Asp-(Et)Tyr-D,L-APmp-NH$_2$;
k) N$^\alpha$-Ac-Cyclo(S,S)-D,L-APmp-Arg-Gly-Asp-Leu-Cys-NH$_2$;
l) N$^\alpha$-Ac-Cyclo(S,S)-Cys-Arg-Gly-Asp-His-Pen-NH$_2$; and
m) Cyclo(S,S)-Mpa-Arg-Gly-Asp-(Me)Ser-Cys-NH$_2$.

Example 47

Preparation of Cyclo(S,S) Cys-MeArg-Gly-Asp-Pen-NH$_2$

Using the method of Example 14, except omitting the acetylation step, the titled compound is prepared.

Example 48

Preparation of N$^\alpha$-PhCO-Cyclo(S,S) Cys-MeArg-Gly-Asp-Pen-NH$_2$

The compound of Example 47 (0.5 mmol) is stirred in methylene chloride and treated with triethylamine (1 mmol) at 0°. Benzoyl chloride (0.6 mmol) is added and the reaction is warmed to room temperature. After 3 hrs. the reaction is diluted with ice water and methylene chloride. The organic layer is separated, washed with water and 5% sodium bicarbonate, and dried over MgSO$_4$. The solvent is evaporated and the residue is chromatographed on a medium pressure ODS reversed-phase column to yield the titled compound.

Using the same procedure, except substituting phenyl acetyl chloride, provides N$^\alpha$-PhCH$_2$CO-Cyclo(S,S) Cys-MeArg-Gly-Asp-Pen-NH$_2$.

Example 49

Preparation of Cyclo(S,S) Cys-MeArg-Gly-Asp-Pen-OH

Using the procedure of 15(c), Boc-Pen(4-MBzl) is coupled to a hydroxymethyl resin (1% crosslinked, 1 g, 1 mmol), using 4-pyrrolidinopyridine (0.15 g, 1 mmol) and DCC (620 mg, 3 mmol) in methylene chloride. Using the procedure of Example 1, Boc-Asp(OBzl), Boc-Gly, Boc-MeArg(Tos) and Boc-Cys(SEt) are coupled, acetylated treated with HF and cyclized to provide the titled compound.

Example 50

Using the methods of synthesis described in detail above, the following compounds are produced:
a) N$^\alpha$-Ac-Cyclo(S,S)-Cys-(α-Et)HArg-Gly-Asp-Cys-NH$_2$;
b) N$^\alpha$-Ac-Cyclo(S,S)-Cys-(α-Bzl)Arg-Gly-Asp-Pen-NH$_2$;
c) N$^\alpha$-Ac-Cyclo(S,S)-D,L-APmp-MeArg-Gly-Asp-Trp-Cys-NH$_2$;
d) N$^\alpha$-Ac-Cyclo(S,S)-Pen-D-HArg-Gly-Asp-D-Tyr-Cys-NH$_2$;
e) N$^\alpha$-Ac-Cyclo(S,S)-Pen-D-(α-Et)Arg-Gly-Asp-(Et)Ser-Cys-NH$_2$;
f) N$^\alpha$-Ac-Cyclo(S,S)-Cys-D-MeArg-Gly-Asp-D-Phe-Cys-NH$_2$;
g) N$^\alpha$-Ac-Cyclo(S,S)-Cys-D-(α-Et)Arg-Arg-Gly-Asp-D-Cys-NH$_2$;
h) Cyclo(S,S)-Mpr-D-(α-Me)His-Arg-Gly-Asp-Cys-NH$_2$;
i) Cyclo(S,S)-Pmp-D-Ala-MeArg-Gly-Asp-Pen-NH$_2$;
j) N$^\alpha$-Ac-Cyclo(S,S)-Pen-(α-Me,Et$_2$)Arg-MeArg-Gly-Asp-Cys-NH$_2$;
k) N$^\alpha$-HCO-Cyclo(S,S)-Cys-(α-Me)Ala-Arg-Gly-Asp(Me)Pen-Cys-NH$_2$;
l) N$^\alpha$-Ac-Cyclo(S,S)-Cys-(Me$_2$)Arg-MeArg-Gly-Asp-Cys-NH$_2$;
m) N$^\alpha$-Ac-Cyclo(S,S)-Cys-(α-Et)Gly-HArg-Gly-Asp-D-Cys-NH$_2$.

n) $N^\alpha$-Ac-Cyclo(S,S)-D-Cys-His-($\alpha$-Me)HArg-Gly-Asp-Cys-NH$_2$; and
o) $N^\alpha$-Ac-Cyclo(S,S)-D-Pen-(a-Me)Abu-Arg-Gly-Asp-D-Pen-NH$_2$.

Example 51

Using the methods of synthesis described in detail above, the following compounds are produced:
a) $N^\alpha$-Ac-His-MeArg-Gly-Asp-D-Ala-NH$_2$;
b) $N^\alpha$-Ac-(Me$_2$)Arg-Arg-Gly-Asp-D-Tyr-NH$_2$;
c) $N^\alpha$-Ac-($\alpha$-Me,Me$_2$)Arg-Gly-Asp-Nal-NH$_2$;
d) $N^\alpha$-Ac-($\alpha$-Me)HArg-Gly-Asp-(Et)Pen-NH$_2$;
e) $N^\alpha$Ac-($\alpha$-Bzl)Arg-Gly-Asp-D-Thr-NH$_2$; and
f) $N^\alpha$-PhCO-MeArg-Gly-Asp-D-Leu-NH$_2$.

Example 52
Parenteral Dosage Unit Composition

A preparation which contains 20 mg of the peptide of Example 1 or 2 as a sterile dry powder is prepared as follows: 20 mg of the peptide is dissolved in 15 ml of distilled water. The solution is filtered under sterile conditions into a 25 ml multi-dose ampoule and lyophilized. The powder is reconstituted by addition of 20 ml of 5% dextrose in water (D5W) for intravenous or intramuscular injection. The dosage is thereby determined by the injection volume. Subsequent dilution may be made by addition of a metered volume of this dosage unit to another volume of D5W for injection, or a metered dose may be added to another mechanism for dispensing the drug, as in a bottle or bag for IV drip infusion or other injection-infusion system.

Example 53
Oral Dosage Unit Composition

A capsule for oral administration is prepared by mixing and milling 50 mg of the peptide with 75 mg of lactose and 5 mg of magnesium stearate. The resulting powder is screened and filled into a hard gelatin capsule.

Example 54
Oral Dosage Unit Composition

A tablet for oral administration is prepared by mixing and granulating 20 mg of sucrose, 150 mg of calcium sulfate dihydrate and the peptide with a 10% gelatin solution. The wet granules are screened, dried, mixed with 10 mg starch, 5 mg talc and 3 mg stearic acid; and compressed into a tablet.

The above description fully discloses how to make and use this invention. This invention, however, is not limited to the precise embodiments described herein, but encompasses all modifications within the scope of the claims which follow.

What is claimed is:
1. A compound of formula (II):

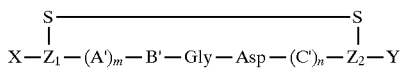

(II) wherein:
A' is a D- or L-amino acid chosen from Arg, HArg, (Me$_2$)Arg, (Et$_2$)Arg, Ala, Gly, His, Abu, Lys or an $\alpha$-R' substituted derivative thereof, or Pro;
B' is an $\alpha$-R' substituted derivative of D- or L-Arg;
C' is a D or L amino acid chosen from Tyr, (Alk)Tyr, Phe, (4'W)Phe, HPhe, Phg, Trp, His, Ser, (Alk)Ser, Thr, (Alk)Thr, (Alk)Cys, (Alk)Pen, Ala, Val, Nva, Met, Leu, lie, Nle, or Nal, or an $\alpha$-R' substituted derivative thereof;
W is halogen or Alk;
Y is NR$_1$R$_2$ or OR$_3$;
R$_1$ and R$_2$ are each independently H, Alk or (CH$_2$)$_p$Ph;
R$_3$ is Alk, (CH$_2$)$_p$Ph or H;
X is R$_4$R$_5$N or H;
R$_4$ is H or Alk;
R$_5$ is H, Alk, HCO, AlkCO, PhCH$_2$ or Ph(CH$_2$)$_q$CO;
R' is Alk or PhCH$_2$;
Z$_1$ is a D- or L-isomer of Cys, Pen or APmp;
Z$_2$ is a D- or L- isomer of Cys, Pen or APmp;
q, m and n are independently 0 or 1; and
p is 0, 1, 2 or 3;
or a pharmaceutically acceptable salt thereof.

2. A compound according to claim 1 which is:
$N^\alpha$-Ac-Cyclo(S,S)Cys-MeArg-Gly-Asp-Ser-Cys-NH$_2$;
$N^\alpha$-Ac-Cyclo(S,S)Cys-MeArg-Gly-Asp-Ser-Pen-NH$_2$;
$N^\alpha$-Ac-Cyclo(S,S)Cys-MeArg-Gly-Asp-(Me)Ser-Cys-NH$_2$;
Cyclo(S,S)Mpr-MeArg-Gly-Asp-Ser-Cys-NH$_2$;
$N^\alpha$-Ac-Cyclo(S,S)Cys-MeArg-Gly-Asp-Cys-NH$_2$;
Cyclo(S,S)Mpr-MeArg-Gly-Asp-Pen-NH$_2$;
$N^\alpha$-Ac-Cyclo(S,S)Cys-MeArg-Gly-Asp-Pen-NH$_2$;
$N^\alpha$-Ac-Cyclo(S,S)Cys-MeArg-Gly-Asp-Tyr-Cys-NH$_2$;
$N^\alpha$-Ac-Cyclo(S,S)Pen-MeArg-Gly-Asp-Pen-NH$_2$;
$N^\alpha$-Ac-Cyclo(S,S)Cys-D-MeArg-Gly-Asp-Pen-NH$_2$.

3. A method for inhibiting platelet aggregation in a mammal comprising administering an effective amount of a peptide according to claim 1, and a pharmaceutically acceptable carrier.

4. A method for inhibiting clot formation in a mammal comprising administering an effective amount of a peptide according to claim 1, and a pharmaceutically acceptable carrier.

5. A method for preventing or treating myocardial infarction in a mammal comprising administering an effective amount of a peptide according to claim 1, and a pharmaceutically acceptable carrier.

6. A method for preventing or treating stroke in a mammal comprising administering an effective amount of a peptide according to claim 1, and a pharmaceutically acceptable carrier.

7. A compound according to claim 1, in which B' is an $\alpha$-R' substituted derivative of Arg.

8. A compound according to claim 1 in which m is 1 and n is 0.

9. A compound according to claim 8 in which B' is MeArg.

10. A compound according to claim 8 in which A' is Gly or Arg.

11. A compound according to claim 1 in which m is 0 and n is 1.

12. A compound according to claim 11 in which C' is Ser, (Me)Ser, Thr, Tyr, Phe, or Nal.

13. A compound according to claim 11 in which B' is MeArg.

14. A compound according to claim 1 in which both m and n are 0 and B' is MeArg.

15. The compound according to claim 2 which is $N^\alpha$-Ac-Cyclo(S,S)Cys-MeArg-Gly-Asp-Ser-Cys-NH$_2$.

16. The compound according to claim 2 which is $N^\alpha$-Ac-Cyclo(S,S)Cys-MeArg-Gly-Asp-Cys-NH$_2$.

17. The compound according to claim 2 which is $N^\alpha$-Ac-Cyclo(S,S)Cys-MeArg-Gly-Asp-Pen-NH$_2$.

18. The compound according to claim 2 which is $N^{\alpha}$-Ac-Cyclo(S,S)Cys-MeArg-Gly-Asp-Tyr-Cys-NH$_2$.

19. A pharmaceutical composition for inhibiting platelet aggregation in a mammal, which comprises an effective amount therefor of a peptide according to claim 1 and a pharmaceutically acceptable carrier.

20. A pharmaceutical composition for inhibiting platelet aggregation in a mammal, which comprises an effective amount therefor of a peptide according to claim 2 and a pharmaceutically acceptable carrier.

21. A pharmaceutical composition for inhibiting platelet aggregation in a mammal, which comprises an effective amount therefor of a peptide according to claim 17 and a pharmaceutically acceptable carrier.

22. A pharmaceutical composition for inhibiting platelet aggregation in a mammal, which comprises an effective amount therefor of a peptide according to claim 17 and a pharmaceutically acceptable carrier.

* * * * *